US011977985B2

(12) United States Patent
Naidoo et al.

(10) Patent No.: US 11,977,985 B2
(45) Date of Patent: May 7, 2024

(54) MACHINE LEARNING TECHNIQUES FOR PREDICTIVE PRIORITIZATION

(71) Applicant: Optum, Inc., Minnetonka, MN (US)

(72) Inventors: Darrel Naidoo, Loughton (GB); Paul J. Godden, London (GB); Gregory J. Boss, Saginaw, MI (US); Peter M. Wahl, Dover, MA (US)

(73) Assignee: Optum, Inc., Minnetonka, MN (US)

( * ) Notice: Subject to any disclaimer, the term of this patent is extended or adjusted under 35 U.S.C. 154(b) by 757 days.

(21) Appl. No.: 17/096,062

(22) Filed: Nov. 12, 2020

(65) Prior Publication Data

US 2022/0147865 A1    May 12, 2022

(51) Int. Cl.
| | | |
|---|---|---|
| G06N 3/0895 | (2023.01) | |
| G06F 16/23 | (2019.01) | |
| G06N 3/045 | (2023.01) | |
| G06N 3/08 | (2023.01) | |
| G06N 3/088 | (2023.01) | |
| G06N 3/09 | (2023.01) | |
| G06N 3/0985 | (2023.01) | |
| G06N 20/00 | (2019.01) | |
| G16H 50/20 | (2018.01) | |

(52) U.S. Cl.
CPC ....... G06N 3/0895 (2023.01); G06F 16/2379 (2019.01); G06N 3/045 (2023.01); G06N 3/08 (2013.01); G06N 3/088 (2013.01); G06N 3/09 (2023.01); G06N 3/0985 (2023.01); G06N 20/00 (2019.01); G16H 50/20 (2018.01)

(58) Field of Classification Search
CPC .......... G06N 20/00; G06N 3/08; G06N 3/088; G06N 3/09; G06N 3/0985; G06N 3/0895; G06N 3/045; G06F 16/2379; G16H 50/20
See application file for complete search history.

(56) References Cited

U.S. PATENT DOCUMENTS

| | | |
|---|---|---|
| 7,983,848 B2 | 7/2011 | Hoffman et al. |
| 8,357,089 B2 | 1/2013 | Scheuner |
| 9,646,262 B2 * | 5/2017 | Phillipps ................. G06N 20/10 |
| 2002/0143578 A1 | 10/2002 | Cole et al. |
| 2003/0113727 A1 | 6/2003 | Gim et al. |
| 2017/0256177 A1 | 9/2017 | Abrahams et al. |
| 2017/0357760 A1 | 12/2017 | Han et al. |
| 2019/0108912 A1 * | 4/2019 | Spurlock, III ..... C07K 16/2866 |

(Continued)

OTHER PUBLICATIONS

Omta, Wienand A., et al. "Combining supervised and unsupervised machine learning methods for phenotypic functional genomics screening." Slas Discovery: Advancing the Science of Drug Discovery 25.6 (2020): 655-664. (Year: 2020).*

(Continued)

*Primary Examiner* — Andrew L Tank
(74) *Attorney, Agent, or Firm* — ALSTON & BIRD LLP

(57) ABSTRACT

Various embodiments of the present invention provide methods, apparatus, systems, computing devices, computing entities, and/or the like for performing predictive prioritization. Certain embodiments utilize systems, methods, and computer program products that perform predictive prioritization using a combination of supervised machine learning models and unsupervised machine learning models that are in turn used to generate target features for a resultant prioritization machine learning model.

20 Claims, 9 Drawing Sheets

(56) References Cited

U.S. PATENT DOCUMENTS

2020/0034761 A1    1/2020    Brown et al.
2021/0398641 A1*  12/2021  Catani .................... G16H 20/60

OTHER PUBLICATIONS

Chowdhury, A.S., et al., "A biomarker ensemble ranking framework for prioritizing depression candidate genes," 2015 IEEE Conference on Computational Intelligence in Bioinformatics and Computational Biology (CIBCB), Niagara Falls, ON, Canada, 2015, pp. 1-6, doi: 10.1109/CIBCB.2015.7300287 (Year: 2015).*
"GTR: Genetic Testing Registry," (2 pages). [article, online]. [Retrieved from the Internet Jan. 28, 2021] <URL: https://www.ncbi.nlm.nih.gov/gtr/>.
Alexion. "Research and Development," (7 pages). [article, online]. [Retrieved from the Internet Jan. 28, 2021] <URL: https://alexion.com/our-research/research-and-development>.
Antoniou, Antonis et al. "Predicting The Likelihood Of Carrying A BRCA1 or BRCA2 Mutation: Validation of BOADICEA, BRCAPRO, IBIS, Myriad and the Manchester Scoring System Using Date From UK Genetics Clinics," Journal of Medical Genetics, vol. 45, (2008), pp. 425-431. DOI: 10.1136/jmg.2007.056556.
Brett, Tom et al. "Screening For Familial Hypercholesterolaemia In Primary Care: Time For General Practice To Play Its Part," Atherosclerosis, vol. 277, (2018), pp. 399-406. DOI: 10.1016/j.atherosclerosis.2018.08.019.
Congenica. "Genomic Analysis Tools—Congenica Clinical Genomics Software," (8 pages). [article, online]. [Retrieved from the Internet Jan. 28, 2021] <URL: https://www.congenica.com/solutions/our-platform/>.
Evans, D. Gareth et al. "Pathology Update To The Manchester Scoring System Based On Testing In Over 4000 Families," Journal of Medical Genetics, vol. 54, (2017), pp. 674-681. DOI: 10.1136/jmedgenet-2017-104584.
Fabric Genomics. "Why Fabric?", (3 pages). [article, online]. [Retrieved from the Internet Jan. 28, 2021] <URL: https://fabricgenomics.com/products/why-fabric/>.
Fuchsberger, Christian et al. "The Genetic Architecture Of Type 2 Diabetes," Nature, vol. 536, vol. 7614, Aug. 4, 2016, (61 pages). Author Manuscript. DOI: 10.1038/nature18642.
Hanchuan, Peng et al. "Feature Selection Based On Mutual Information Criteria Of Max-Dependency, Max-Relevance, and Min-Redundancy," in IEEE Transactions on Pattern Analysis and Machine Intelligence, vol. 27, No. 8, Aug. 2005, pp. 1226-1238. DOI: 10.1109/TPAMI.2005.159.
Hu, Chunling et al. "Association Between Inherited Germline Mutations in Cancer Predisposition Genes and Risk of Pancreatic Cancer," The Journal of the American Medical Association, vol. 319, No. 23, (2018), pp. 2401-2409. DOI: 10.1001/jama.2018.6228.
Jaffee, Elizabeth M. et al. "Future Cancer Research Priorities In The USA: A Lancet Oncology Commission," Lancet Oncology, vol. 18, No. 11:e653-e706, Nov. 2017, pp. 1-120. Author Manuscript. DOI: 10.1016/S1470-2045(17)30698-8.
Jeon, Jihyoun et al. "Determining Risk of Colorectal Cancer and Starting Age of Screening Based On Lifestyle, Environmental, and Genetic Factors," Gastroenterology, vol. 154, No. 8, (2018), (24 pages). Author Manuscript. DOI: 10.1053/j.gastro.2018.02.021.
McPherson, Elizabeth. "Genetic Diagnosis and Testing In Clinical Practice," Clinical Medicine & Research, vol. 4, No. 2, (2006), pp. 123-129.
Medtronic. "The Guardian™ Connect System," (5 pages). [article, online]. [Retrieved from the Internet Jan. 28, 2021] <https://www.medtronicdiabetes.com/products/guardian-connect-continuous-glucose-monitoring-system>.
Scikit-learn: Machine Learning in Python. "1.13. Feature Selection," Journal of Machine Learning Research, (4 pages). [article, online]. [Retrieved from the Internet Jan. 28, 2021] <https://scikit-learn.org/stable/modules/feature_selection.html>.
SOPHiA. "SOPHiA For Genomics," (4 pages). [article, online]. [Retrieved from the Internet Jan. 28, 2021] <URL: https://www.sophiagenetics.com/en_US/sophia-ai/genomics.html>.
Szender, J. Brian et al. "Breadth of Genetic Testing Selected By Patients At Risk Of Hereditary Breast and Ovarian Cancer," International Journal of Gynecologic Cancer, vol. 28, No. 1, Jan. 2018, (13 pages). Author Manuscript. DOI: 10.1097/IGC.0000000000001122.
Tempus. "Analytic Tools," (5 pages). [article, online]. [Retrieved from the Internet Jan. 28, 2021] <URL: https://www.tempus.com/analytics-tools/>.
The White House. "The Precision Medicine Initiative," (2016), (11 pages). [article, online]. [Retrieved from the Internet Jan. 28, 2021] <URL: https://obamawhitehouse.archives.gov/precision-medicine>.
Willoughby, Ava et al. "Genetic Testing To Guide Risk-Stratified Screens For Breast Cancer," Journal of Personalized Medicine, vol. 9, No. 1, (2019), pp. 1-22. DOI: 10.3390/jpm9010015.
Chowdhury, Abu Sayed et al. "A Biomarker Ensemble Ranking Framework For Prioritizing Depression Candidate Genes," 2015 IEEE Conference on Computational Intelligence in Bioinformatics and Computational Biology (CIBCB), Aug. 12-15, 2015, pp. 1-6, DOI: 10.1109/CIBCB.2015.7300287.
Joachims, Thorsten. "Optimizing Search Engines Using Clickthrough Data," In Proceedings of the Eighth ACM SIGKDD International Conference On Knowledge Discovery and Data Mining, pp. 133-142, Jul. 23, 2002.

* cited by examiner

| MEMBER ID | Medical Name |
|---|---|
| 9345678 | John Smith |

RECOMMENDED GENETIC TESTING SCHEDULE

Lung Cancer  >>  Huntington's Disease  >>  Cystic Fibrosis

MACHINE LEARNING TECHNIQUES FOR PREDICTIVE PRIORITIZATION

BACKGROUND

Various embodiments of the present invention address technical challenges related to performing predictive prioritization. Existing predictive data analysis systems are ill-suited to efficiently and reliably perform predictive prioritization. Various embodiments of the present address the shortcomings of the predictive data analysis systems and disclose various techniques for efficiently and reliably performing predictive prioritization.

BRIEF SUMMARY

In general, embodiments of the present invention provide methods, apparatus, systems, computing devices, computing entities, and/or the like for performing predictive prioritization. Certain embodiments utilize systems, methods, and computer program products that perform predictive prioritization using a combination of supervised machine learning models and unsupervised machine learning models that are in turn used to generate target features for a resultant prioritization machine learning model.

In accordance with one aspect, a method is provided. In one embodiment, the method comprises: identifying, by one or more processors, a plurality of feature data objects for a plurality of predictive data entities; generating, by the one or more processors, a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features; generating, by the one or more processors, a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features; generating, by the one or more processors, a predicted prioritization score for each predictive data entity of the plurality of predictive data entities based at least in part on the multi-dimensional unsupervised machine learning space; and performing, by the one or more processors, one or more prediction-based actions based at least in part on each predicted prioritization score for a predictive data entity of the plurality of predictive data entities.

In accordance with another aspect, a computer program product is provided. The computer program product may comprise at least one computer-readable storage medium having computer-readable program code portions stored therein, the computer-readable program code portions comprising executable portions configured to: identify a plurality of feature data objects for a plurality of predictive data entities; generate a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features; generate a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features; generate a predicted prioritization score for each predictive data entity of the plurality of predictive data entities based at least in part on the multi-dimensional unsupervised machine learning space; and perform one or more prediction-based actions based at least in part on each predicted prioritization score for a predictive data entity of the plurality of predictive data entities.

In accordance with yet another aspect, an apparatus comprising at least one processor and at least one memory including computer program code is provided. In one embodiment, the at least one memory and the computer program code may be configured to, with the processor, cause the apparatus to: identify a plurality of feature data objects for a plurality of predictive data entities; generate a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features; generate a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features; generate a predicted prioritization score for each predictive data entity of the plurality of predictive data entities based at least in part on the multi-dimensional unsupervised machine learning space; and perform one or more prediction-based actions based at least in part on each predicted prioritization score for a predictive data entity of the plurality of predictive data entities.

BRIEF DESCRIPTION OF THE DRAWINGS

Figure 1:
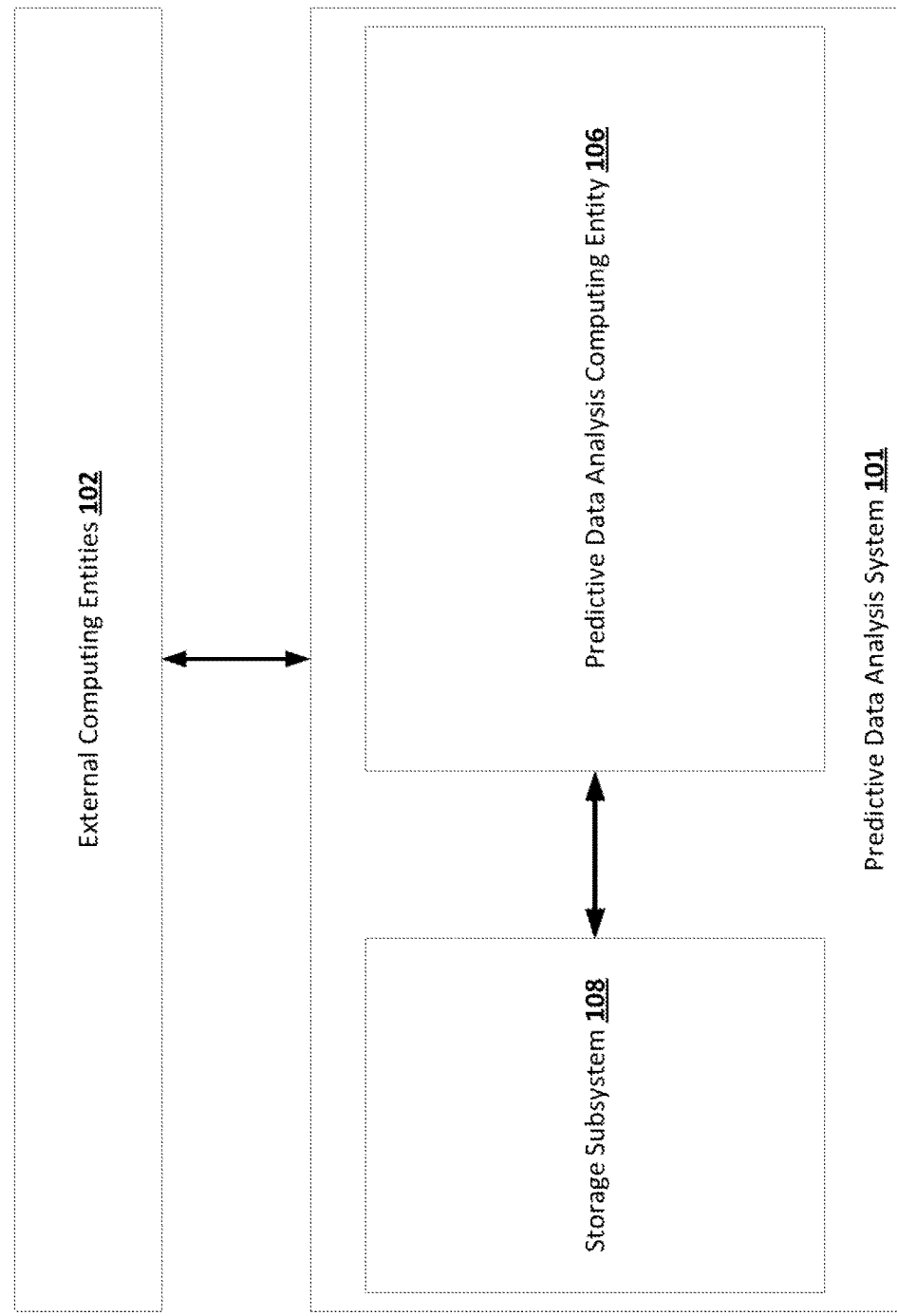

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
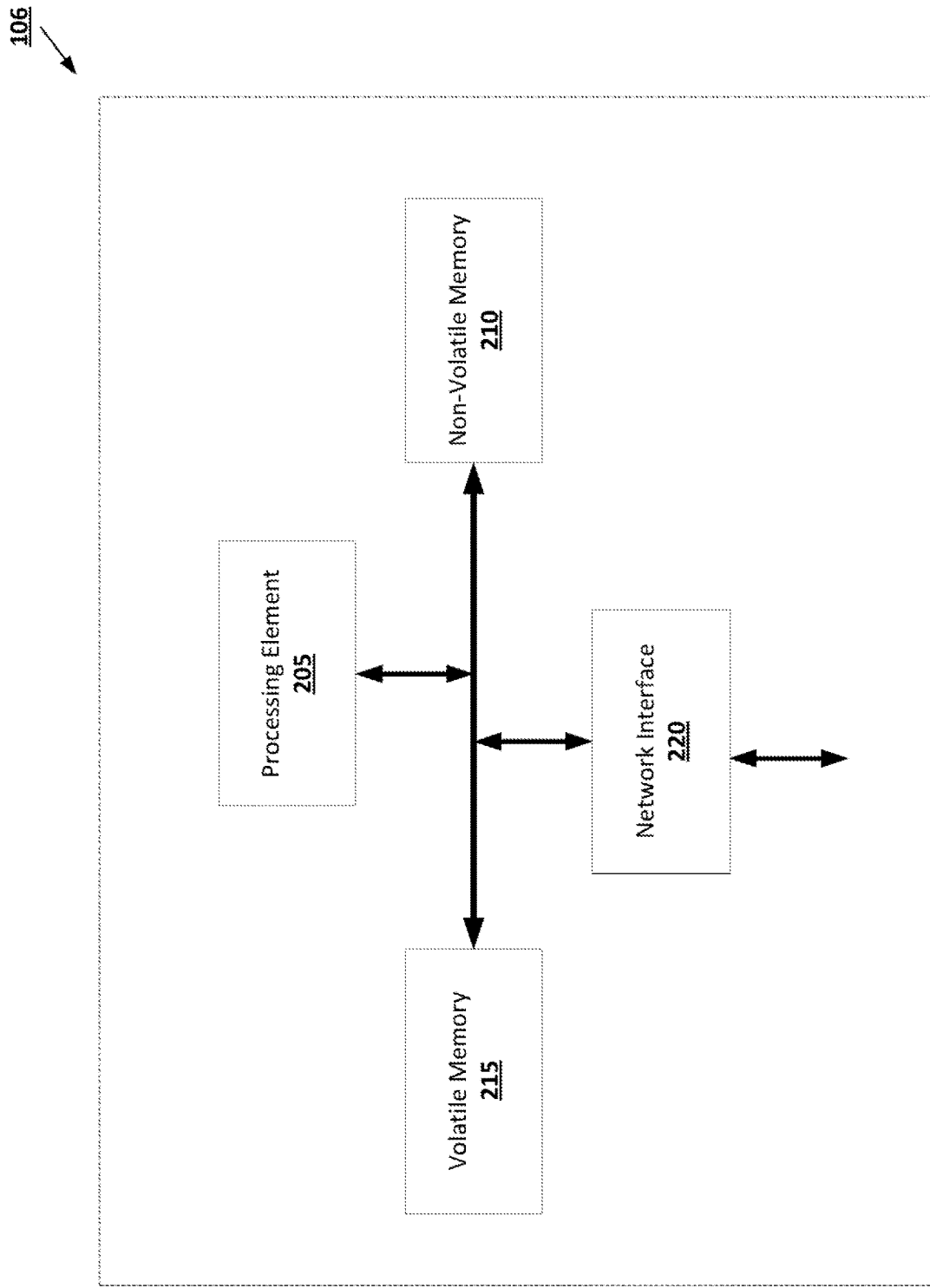

FIG. 2 provides an example predictive data analysis computing entity in accordance with some embodiments discussed herein.

Figure 3:
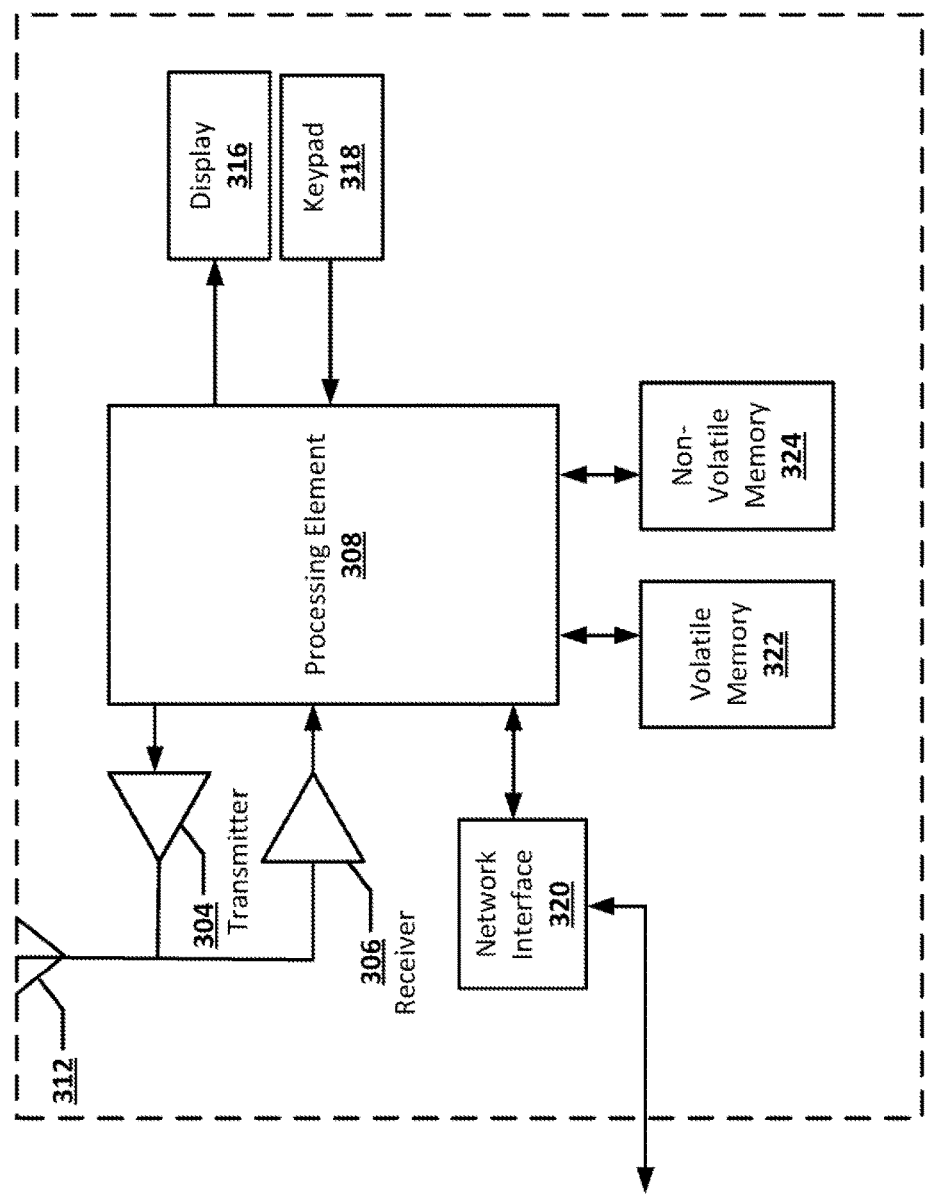

FIG. 3 provides an example external computing entity in accordance with some embodiments discussed herein.

Figure 4:
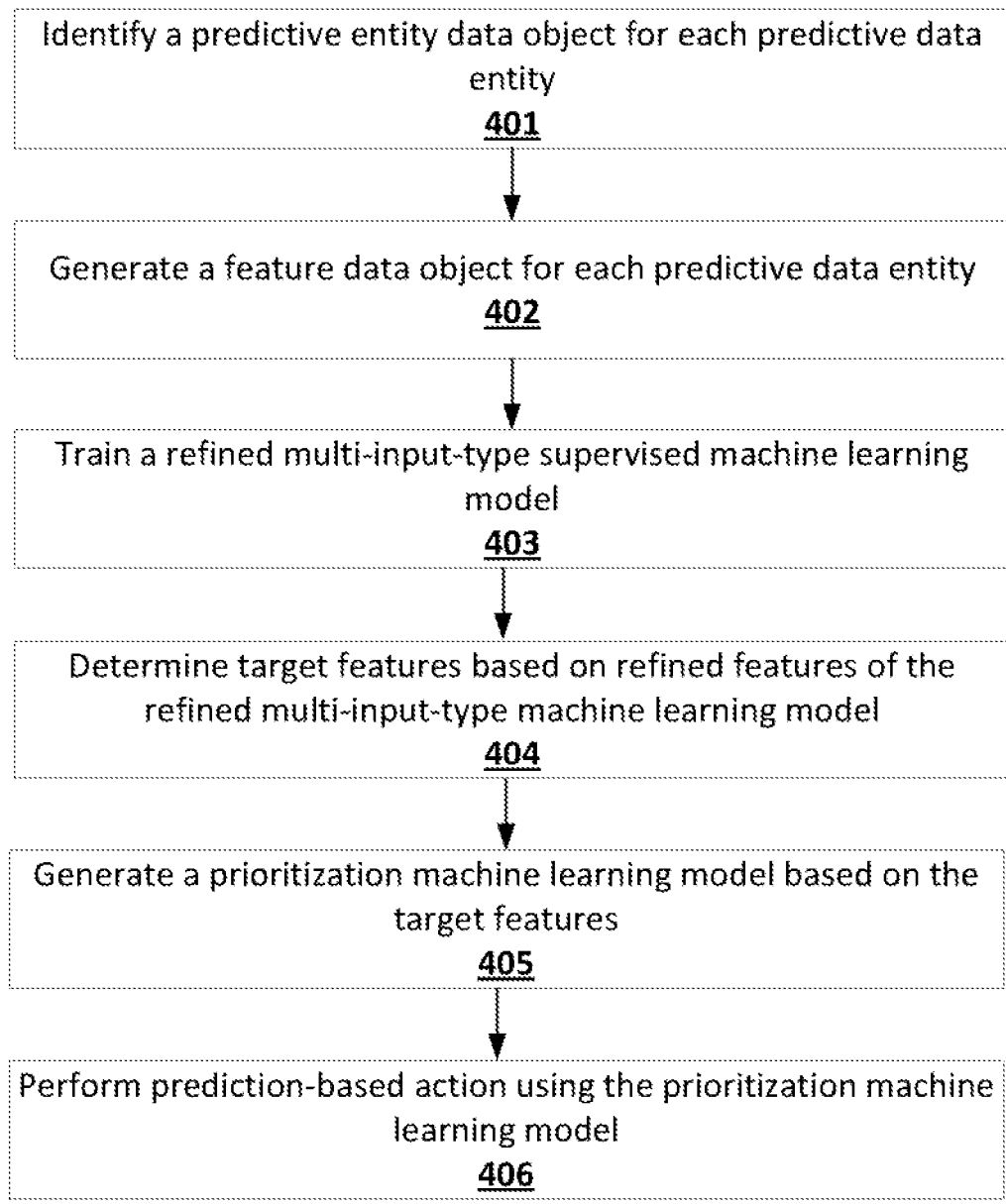

FIG. 4 is a data flow diagram of an example process for hybrid predictive prioritization of a plurality of predictive data entities in accordance with some embodiments discussed herein.

Figure 5:
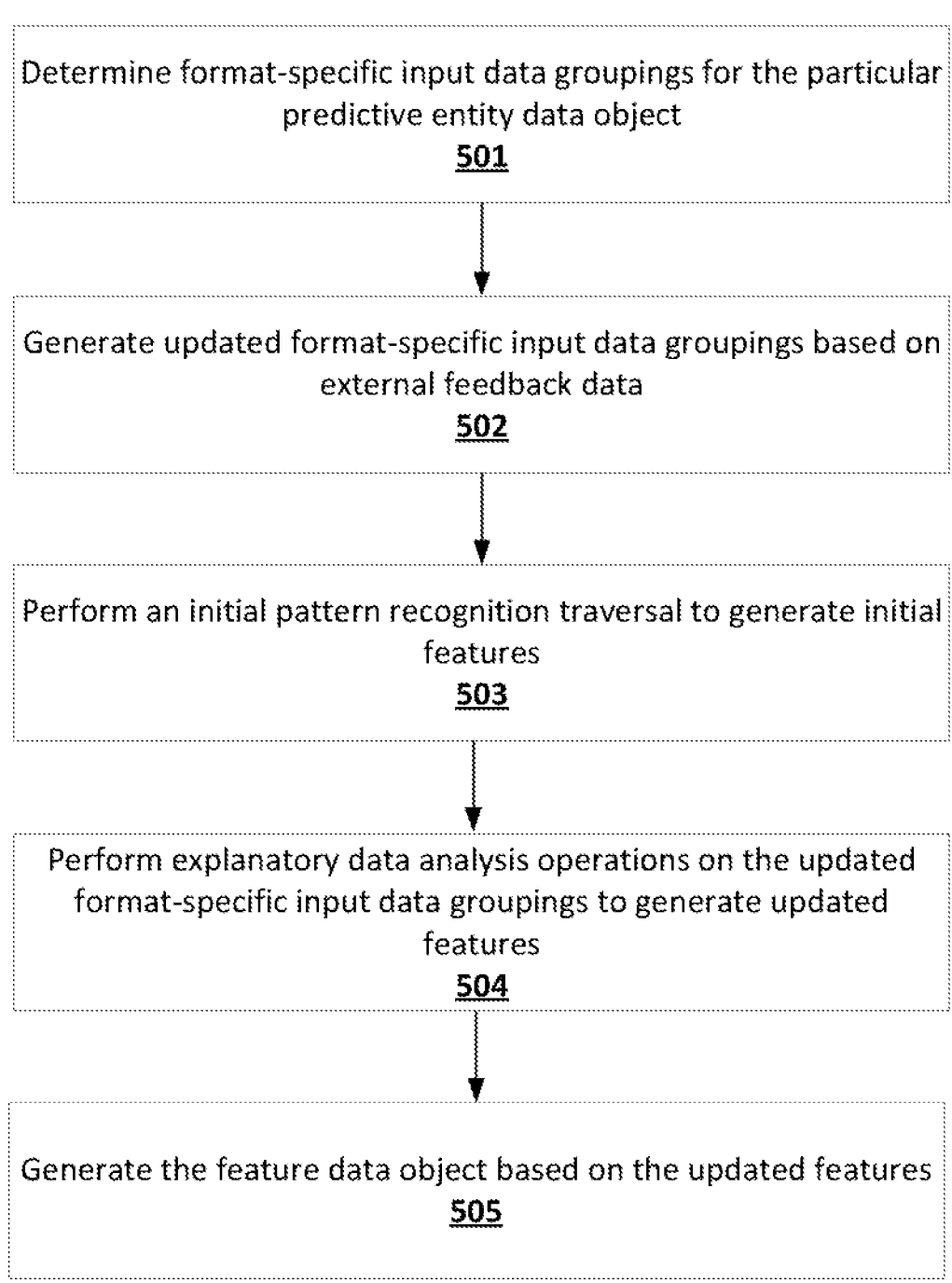

FIG. 5 is a data flow diagram of an example process for generating a feature data object for a predictive data entity in accordance with some embodiments discussed herein.

Figure 6:
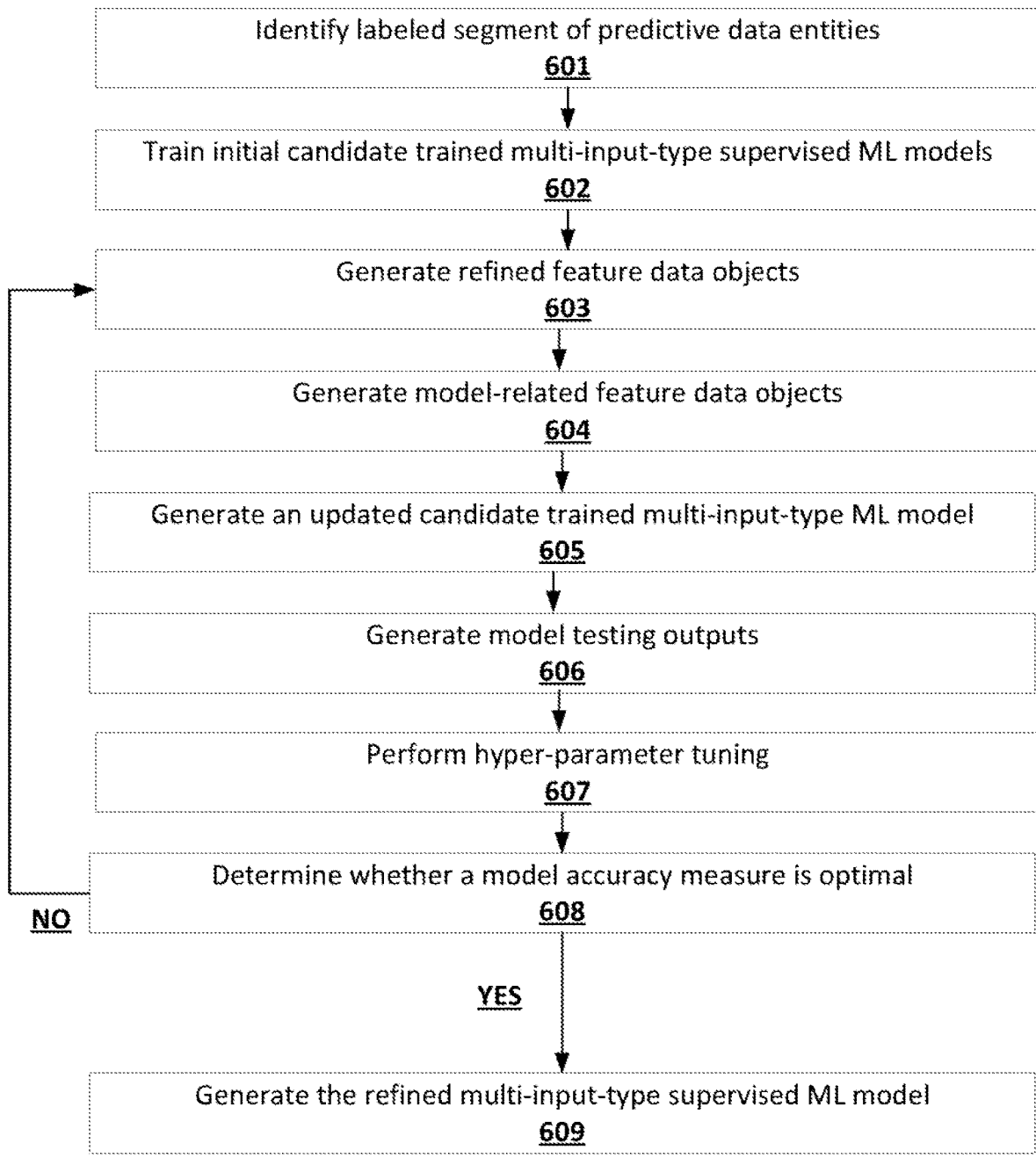

FIG. 6 is a data flow diagram of an example process for generating a refined multi-input-type supervised machine learning model in accordance with some embodiments discussed herein.

Figure 7:
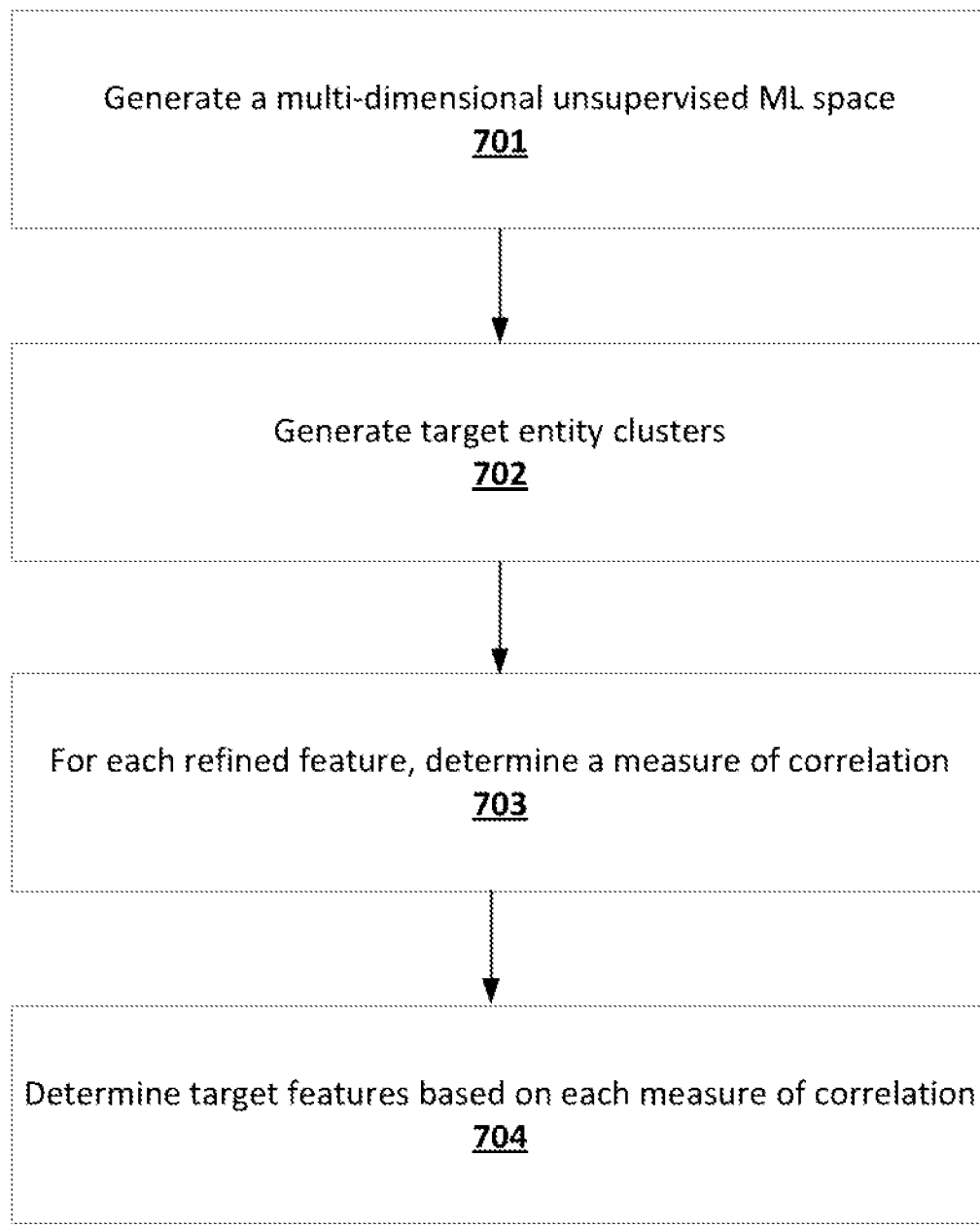

FIG. 7 is a data flow diagram of an example process for determining target features for predictive prioritization based at least in part on refined features associated with a refined multi-input-type supervised machine learning model in accordance with some embodiments discussed herein.

Figure 8:
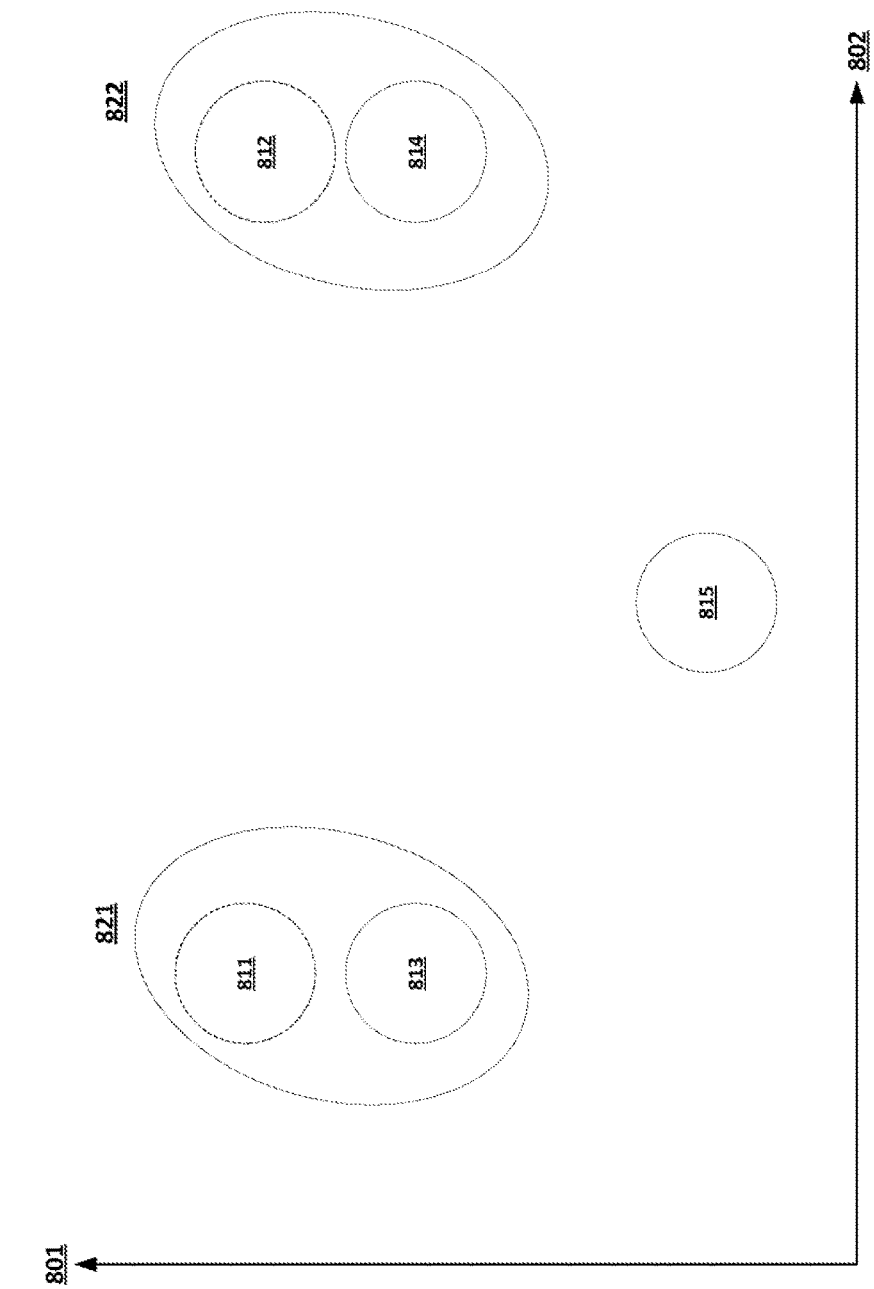

FIG. 8 provides an operational example of a multi-dimensional unsupervised machine learning space for predictive prioritization in accordance with some embodiments discussed herein.

FIG. 9 provides an operational example of a prediction output user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Various embodiments of the present invention disclose techniques for performing predictive prioritization that utilize the combination of a supervised trained machine learning model and an unsupervised trained machine learning model to infer relationships between key target features that are estimated to be highly descriptive of optimal prioritization of predictive data entities. These inferred relationships are then used in some embodiments to generate computationally inefficient prioritization machine learning models that are able to efficiently and reliably predict optimal prioritization schemes for predictive data entities. Two of the key technical advantages of the noted techniques relate to: (i) the efficiency advantage resulting from eliminating the need for using the supervised trained machine learning model and the unsupervised trained machine learning model post training, and (ii) the reliability advantage resulting from using both supervised learning and unsupervised learning to learn cross-feature relationships and feature refinements, which in turn enables learning predictive patterns even when using small amounts of labeled training data.

With respect to the first technical advantage noted above, it is notable that various embodiments of the present invention utilize supervised learning techniques and unsupervised learning techniques to infer target features that are then used to generate a resultant model, where it is this resultant model and not the underlying supervised models and unsupervised models that are run post-training and during a predictive inference. In various embodiments, after training and during a predictive inference, there is no need to execute computationally costly machine learning operations; instead, the resultant model (which may be in some embodiments a linear model or a computationally efficient non-linear model) is used to generate predicted prioritization scores used to perform predictive prioritization. Thus, by utilizing supervised learning techniques and unsupervised learning techniques to infer target features that are then used to generate a resultant model and performing predictive prioritization post-training using the noted resultant model, various embodiments of the present invention reduce the need to perform computationally costly machine learning operations post-training, thus reducing the amount of processing power needed to perform predictive prioritization after training of the resultant model. This in turn means that various embodiments of the present invention reduce the computational complexity of performing machine-learning-based predictive prioritization and make important technical contributions to improving computational efficiency of performing predictive prioritization as well as to the fields of machine learning and predictive data analysis.

With respect to the second technical advantage noted above, various embodiments of the present invention use supervised learning on limited training data to refine features that are then used by an unsupervised learning technique to infer cross-feature relationships. The result is a powerful framework that is capable of performing reliable and accurate predictive prioritization even when limited labeled training data is available, for instance in relation to genetic test prioritization where limited ground-truth data about output of previous genetic tests is available. Thus, by utilizing supervised learning on limited training data to refine features that are then used by an unsupervised learning technique to infer cross-feature relationships, various embodiments of the present invention enable reliable and accurate predictive prioritization even when limited labeled training data is available, a feature that improves reliability and accuracy of performing machine-learning-based predictive prioritization and makes further important technical contributions to the fields of machine learning and predictive data analysis, especially with respect to the important and insufficiently explored problem of predictive prioritization of predictive data entities.

An important application of various embodiments of the present invention relates to genetic test prioritization. Aspects of the genetic test prioritization concepts of the present invention are described in greater detail below.

For much of the history of medicine, the approach to treatment selection for an individual patient has not been based upon their individual physiology, but instead on an evidence-based paradigm that reflects on an "average patient." However, since the completion of the Human Genome Project in 2003, the possibility to implement truly personalized medicine, based upon each patient's unique genetic profile, became a possibility and a means by which to transform healthcare positively. In the United States this was formally initiated in 2015 when President Obama launched the Precision Medicine Initiative. Today, the promise of improving diagnostic accuracy, identifying patients with a definitive clinical need, and ensuring that the most suitable drugs for a given patient's genetic profile are administered remains a work-in-progress due to the complexity of such a radical change in clinical practice.

An essential part of any application of precision medicine is to perform genetic testing on patients, either to accurately diagnose a specific condition and thus intervene early for best benefit, or to optimize the choice of drug treatment. Currently, there does not exist methods for stratifying patients into prioritized cohorts for genetic testing. For certain diseases or conditions, there are potentially massive benefits for prioritizing genetic testing as certain conditions are difficult to diagnose and have a high associated mortality rate—e.g. pancreatic cancer—and thus molecular profiling via genetic testing would permit precision medicine-based approaches to be utilized as early interventions and to improve care and outcomes.

With a wealth of Electronic Medical Record (EMR) data available from hospitals and care providers, high-quality de-identified medical claims data, socio-economic data and behavioral data, all of which could provide insights in order to determine which patients would most likely benefit from genetic testing, the key questions become: how could such data be used to determine patients with clinical needs which would benefit from genetic testing, and which patients should be tested as a clinical need? As a corollary, the Genetic Testing Registry (https://www.ncbi.nlm.nih.gov/gtr/) lists over 65,000 tests at the time of writing and so the complexity of the problem to be solved is also compounded by the need to determine which test is appropriate for the disease under consideration, i.e. a whole genome sequence or a panel test for specific genetic variants? It is also notable that genetic testing is not necessarily reimbursed through insurance schemes and thus having guidance to ensure those patients for whom priority testing can be ascertained is an important financial factor. Thus, consideration of the clinical utility for a given test for a specific condition is also an open problem to be solved.

Various embodiments of the present invention relate to performing the below operations: (1) a specific disease or condition is selected; (2) for that disease, longitudinal EMR data, claims, socio-economic, prescription and any other appropriate source of data that are available and relevant to search for corresponding identifiers for other known risk factors (e.g. proxies that correspond to variants of the EGFR gene in lung cancer) are processed; (3) if there are sufficient patients within the selected cohort who have "wearable" Internet-of-Things (IoT) data available, e.g. diabetic patients who have their glucometer data recorded periodically via a glucometer, as the data from these devices could be used to compliment other clinical data available for the analyses; (4) using a machine learning application to search through EMR data to determine potential correlations between patient data and known genetic/polygenetic risk across all tumor types, where EMR data may be supplemented by social determinants of health (SDOH) data were possible (e.g. deprivation indices); (5) the system will then through EMR and SDOH data for a given confirmed diagnosis of a specific disease type—e.g. NSCLC—and then, assuming Estimated Glomerular Filtration Rate (EGFR) status is known, will then learn approximate correspondences to indicate potential patients that would most benefit from that specific genetic test (e.g. a panel).

Various embodiments of the present invention also add a feedback loop: the system will learn from its recommendations by receiving input after the patients it recommended for genetic testing had their sequencing performed and received the outcome of the test results. Thus, the system can update and refine its accuracy from the ground truth results of its predictions. Various embodiments of the present invention identify those at risk by generating risk scores to highlight those patients at highest risk and who would benefit from genetic testing as a priority. This may require two steps: firstly, analysis of existing clinical data—such as natural language parsing of PubMed abstracts and relevant research papers for the condition under scrutiny, to derive a prioritization scoring algorithm; and secondly, refinement of the algorithm, using selected data elements, in order to provide a risk score, via a test-and-refine approach until desired accuracy is achieved. Moreover, final review with clinical experts and analysis of typical diagnostic tests and pathways associated with the specified condition, will enable the optimization of sequencing the associated diagnostic tests for a given output prioritizations score.

Various embodiments of the present invention integrate the following features/advantages: starting an assessment of EMR/EHR data for variables that are associated with the condition under consideration (e.g. Alzheimer's disease); determining, via supervised machine learning methods, which variables have associations with the disease in question (this may be accomplished by using both positive and negative cases, i.e. patients that are recorded in the EMR as having the condition, as well as those for whom the condition is absent); applying a second, unsupervised, machine learning method to cluster variables associated with the disease condition; determining a scoring algorithm analogous to the Manchester Risk Score, and implementing this to the variables in question in order to categories patients who should have genetic tests as a priority (the scoring algorithms, and the subsequent thresholds for prioritizing testing, may be derived in close consultation with clinical experts); ensuring that patients undergoing genetic testing for the condition in question have the results fed back in to the system via a feedback loop in order to refine accuracy and ensure the system updates to provide the best possible prioritizations (in other words, if the algorithm does quite not exhibit the desired accuracy then update the variables used and re-check until the optimal score is created (e.g. a using a lifelong learning implementation)); and once the scoring algorithm for each disease under consideration meets sufficient requirements and clinical utility, providing the ability to optimize the sequence of tests—in order to achieve clinical utility and cost savings by not performing unnecessary or duplicated clinical tests—will be determined in collaboration with clinical experts. Using the latter technique, various embodiments of the present invention can provide clinical decision support in order to not only indicate which patients would benefit from priority genetic testing but also the order in which the selected tests should be performed. As one example, it may not be necessary to have a chest X-ray if a genetic panel test indicates that the condition for which a differential diagnosis is in question indicates that it is not a respiratory issue. Moreover, various embodiments of the present invention further enable flagging patients for which an established predictor variable is missing, and prompting clinical staff to acquire that variable from the appropriate test, so that the algorithm can be completed for that patient.

II. Definitions

The term "predictive data entity" may refer to a data object that is configured to describe a real-world entity and/or a virtual entity about which one or more predictive data analysis inferences are generated using a predictive prioritization process. For example, a predictive data entity may describe a patient predictive data entity whose corresponding patient predictive entity data object is processed using a hybrid predictive prioritization process in order to generate at least one of the following predictive data analysis inferences: (i) one or more predicted prioritization scores that each describe an inferred relative significance of administering a corresponding genetic test for a corresponding medical condition to the patient associated with the patient predictive data entity, and (ii) a predicted recommended ordering of each genetic test that is deemed applicable/recommended for the patient associated with the patient predictive data entity based at least in part on each predicted prioritization score associated with the patient predictive data entity.

The term "predictive entity data object" may refer to a data object that is configured to describe one or more data fields associated with a corresponding predictive data entity, where the one or more data fields may be processed by a predictive prioritization process in order to generate one or more predictive data analysis inferences for the corresponding predictive data entity. For example, given a predictive data entity that describes a patient predictive data entity, the predictive entity data object for the patient predictive data entity may describe one or more data fields associated with the patient predictive data entity that are processed using a hybrid predictive prioritization process in order to generate at least one of the following predictive data analysis inferences: (i) one or more predicted prioritization scores that each describe an inferred relative significance of administering a corresponding genetic test for a corresponding medical condition to the patient associated with the patient predictive data entity, and (ii) a predicted recommended ordering of each genetic test that is deemed applicable/recommended for the patient associated with the patient predictive data entity based at least in part on each predicted prioritization score associated with the patient predictive data entity. In the noted example, the predictive entity data object may describe at least one of the following: EMR data associated with the patient predictive data entity, medical claim data associated with the patient predictive data entity, prescription history data associated with the patient predictive data entity, medical history data associated with the patient predictive data entity, demographic profile data associated with the patient predictive data entity, socioeconomic profile data associated with the patient predictive data entity, activity recording data associated with the patient predictive data entity (such as activity recording data associated with associated with the patient predictive data entity that are captured using one or more activity recording wearable devices associated with the patient predictive data entity), family medical history data associated with the patient predictive data entity, blood test result data associated with the patient predictive data entity, diagnosis data associated with the patient predictive data entity, biomarker data associated with the patient predictive data entity, medication history data associated with the patient predictive data entity, comorbidity data associated with the patient predictive data entity, glucometer data associated with the patient predictive data entity (such as glucometer data recorded using a glucometer device such as a Medtronic Guardian Connect System device associated with the patient predictive data entity), medical cohort characterization data associated with the patient predictive data entity, medical note data associated with the patient predictive data entity, medical imaging data associated with the predictive data entity, clinical data associated with the patient predictive data entity, data describing correspondence of the patient associated with the patient predictive data entity with one or more observed/recorded/preconfigured medical patterns (e.g., data describing that the patient associated with the patient predictive data entity is a male patient between 18 and 75 inclusive and that the male patients between the noted age range have a higher likelihood of non-small cell lung cancer), and/or the like.

The term "feature data object" may refer to a data object that is configured to describe the feature values associated with a predictive data entity that are inferred based at least in part on the predictive entity data object for the predictive data entity and that may be used to train a supervised machine learning model (e.g., a multi-input-type supervised machine learning model) that is configured to detect a likelihood of presence of a target predictive condition (e.g., a target medical condition) with respect to the predictive entity. In some embodiments, the feature data object includes a refined feature value for each refined value, where the refined feature value describes extent to which the predictive entity data object associated with the feature data object describes a data pattern associated with the corresponding refined feature that is associated with the refined feature. For example, an exemplary feature data object may describe a one-hot-encoding feature value for each refined feature. In some embodiments, the feature data object for a corresponding predictive entity data object that is in turn associated with a corresponding predictive data entity includes at least one of the following: (i) feature values associated with one or more features whose missing value count/ratio fails to exceed a missing value threshold value, (ii) image data in the corresponding predictive entity data object (which may for example be supplied as an input to an image processing model, such as a depth-wise searchable convolutional neural network model), and/or image metadata inferred based at least in part on image data in the corresponding predictive entity data object, (iii) unstructured data in the corresponding predictive entity data object that may be used to generate features that may be supplied as an input to a recurrent neural network, and (iv) other features values related to features deemed important based at least in part on the results of data engineering operations and/or based at least in part on external data such as SME data. In some embodiments, the feature data object may include various per-model segments that each is configured to be supplied as an input to a different per-input-type component of a multi-input-type supervised machine learning model. For example, the feature data object may include an image-based segment that is configured to be supplied to an image processing component of a multi-input-type supervised machine learning model, such as an image processing component that includes an image processing model, e.g., a depth-wise searchable convolutional neural network model. As another example, the feature data object may include an unstructured segment that is configured to be supplied to an unstructured data processing component of a multi-input-type supervised machine learning model, e.g., an unstructured data processing component that includes an unstructured data processing model, such as a recurrent neural network including a Long Short Term Memory (LSTM) RNN. As yet another example, the feature data object may include a structured segment that is configured to be supplied to a structured data processing component of a multi-input-type supervised machine learning model, such as a structured data processing component that includes an structured data processing model, e.g., a fully connected feed-forward neural network.

The term "multi-input-type supervised machine learning model" may refer to a data object that describes parameters and/or hyper-parameters of a machine learning model that is configured to process feature data objects including features extracted from two or more input data formats and/or two or more input data types in order to generate a supervised machine learning outputs for a group of predictive data entities. In some embodiments, the feature data object may include various per-model segments that each is configured to be supplied as an input to a different per-input-type component of a multi-input-type supervised machine learning model. For example, the feature data object may include an image-based segment that is configured to be supplied to an image processing component of a multi-input-type supervised machine learning model, such as an image processing component that includes an image processing model, e.g., a depth-wise searchable convolutional neural network model. As another example, the feature data object may include an unstructured segment that is configured to be supplied to an unstructured data processing component of a multi-input-type supervised machine learning model, such as an unstructured data processing component that includes an unstructured data processing model, e.g., a recurrent neural network including a Long Short Term Memory (LSTM) RNN. As yet another example, the feature data object may include a structured segment that is configured to be supplied to a structured data processing component of a multi-input-type supervised machine learning model, such as a structured data processing component that includes an structured data processing model, e.g., a fully connected feedforward neural network. However, while various embodiments of the present invention describe training a multi-input-type supervised machine learning model, a person of ordinary skill in the relevant technology will recognize that various inventive techniques disclosed herein may be implemented using a single-input-type machine learning model.

The term "format-specific input data grouping" may refer to a data object that is configured to describe a subset of the input data described by a corresponding predictive entity data object that has a particular data modeling format and/or data type format. For example, the predictive entity data object for a particular patient predictive data entity may be divided into the following format-specific input data groupings: a first format-specific input data grouping that includes image data (e.g., medical image data) associated with the patient predictive data entity, a second format-specific input data grouping that describes unstructured data (e.g., clinical note data, medical note data, patient medical journal data, and/or the like) associated with the patient predictive data entity, a third format-specific input data grouping that describes structured data (e.g., blood test report data, activity recording data, diagnosis data, prescription history data, and/or the like) associated with the patient predictive data entity, and a fourth format-specific input data grouping that describes non-physiological and/or supplemental data (e.g., demographic profile data, socioeconomic profile data, and/or the like) associated with the patient predictive data entity. In some embodiments, one objective of dividing input data associated with a predictive entity data object into format-specific input data groupings is to facilitate integration of external feedback data into each format-specific input data grouping by directing each format-specific input data grouping to external feedback agents (e.g., subject matter expert (SME) agents) that are deemed to have particular expertise/background in matters pertaining to the format-specific input data grouping.

The term "external feedback data" may refer to a data object describing data provided by an external feedback agent (e.g., a subject matter expert (SME) agent) that is configured to be integrated into a predictive entity data object as part of a data engineering operation. In some embodiments, to integrate external feedback data (e.g., SME data) into a format-specific input data grouping to generate an updated format-specific input data grouping, a predictive data analysis computing entity provides the format-specific input data grouping to an external feedback agent, receives refinement/amendment data from the external feedback agent, and integrate the refinement/amendment data to the format-specific input data grouping. Examples of external feedback agents include clinical experts, such as medical imaging experts, medical notes experts, demographic profile experts, and/or the like. In some embodiments, the external feedback data for a corresponding format-specific input data grouping is configured to highlight deficiencies, omissions, and/or errors in the corresponding format-specific input data grouping, and the predictive data analysis computing entity is configured to refine/amend the corresponding format-specific input data grouping by adding omitted features into the format-specific input data grouping as well as removing or replacing deficient/error-prone features from the format-specific input data grouping.

The term "initial feature" may refer to a data object that is configured to describe a feature of a predictive entity data object that is determined using an initial pattern recognition traversal of the predictive entity data object. In some embodiments, to perform the initial pattern recognition traversal of an updated format-specific input data grouping to detect a set of initial features for the updated format-specific input data grouping, a predictive data analysis computing entity searches the updated format-specific input data grouping to detect whether the updated format-specific input data grouping describes one or more data patterns that are deemed correlated with a target medical condition. For example, to detect whether an updated format-specific input data grouping describes known risk factors associated with the tumor expressing PD-L1, the predictive data analysis computing entity may detect whether the updated format-specific input data grouping describes that a corresponding patient predictive data entity is associated with at least one of the following: epidermal growth factor receptor (EGFR) mutations in lung adenocarcinomas, elevated spirometry, persistent cough, above-65 age, and/or the like.

The term "updated feature" may refer to a data object that is configured to describe a feature of a predictive entity data object that is determined by performing one or more explanatory data analysis operations on the predictive entity data object. In some embodiments, a predictive data analysis computing entity performs one or more explanatory data analysis operations on the updated format-specific input data groupings using the set of initial features to generate one or more updated features for the particular predictive entity data object. In some embodiments, to perform the one or more explanatory data analysis operations on the updated format-specific input data groupings to generate one or more updated features for the particular predictive entity data object, the predictive data analysis computing entity performs the following operations: (i) for each initial feature in the set of initial features for an updated format-specific input data grouping, generating a numerical representation value such as a one-hot-coding categorical variable representation, (ii) processing the numerical representation values for the initial features across all of the plurality of predictive data entities using a cross-feature collinearity detection model to detect co-linearities across the numerical representations and consolidate the set of initial features to reduce cross-feature co-linearities, and (iii) processing the numerical representation values for the consolidated features across all of the plurality of predictive data entities using a feature deficiency detection machine learning model to detect defective features having an above-threshold count/ratio of missing values and removing the defective features from the consolidated features to generate the updated features. For example, consider a set of initial features that includes features $F_1$, $F_2$, $F_3$, and $F_4$. By processing numerical representations for the set of initial features across all of the plurality of predictive data entities using a cross-feature collinearity detection model, the predictive data analysis computing entity may first determine that the features $F_1$ and $F_2$ are co-linear. To address this cross-feature co-linearity, the predictive data analysis computing entity 106 may remove $F_1$ from the set of initial features to generate a set of consolidated features that includes $F_2$, $F_3$, and $F_4$. Afterward, the predictive data analysis computing entity may process the numerical representation values for the consolidated features across all of the plurality of predictive data entities using a feature deficiency detection machine learning model to detect that $F_4$ has an above-threshold count/ratio of missing values. To address this feature value deficiency, the predictive data analysis computing entity 106 may remove $F_4$ from the set of initial features to generate a set of updated features that includes $F_2$ and $F_3$.

The term "ground-truth prediction" may refer to a data object describing an observed/recorded label associated with a corresponding predictive data entity that describes whether the predictive data entity is deemed to associated with a target predictive condition for the ground-truth prediction. For example, the ground-truth prediction for a particular patient predictive data entity may describe whether the particular patient predictive data entity has been observed/recorded to have a particular diagnosis, such as a diagnosis for non-small-cell lung carcinoma (NSCLC). As another example, the ground-truth prediction for a particular patient predictive data entity may describe whether the particular patient predictive data entity has been observed/recorded to have been tested positive for a particular condition such as NSCLC. As yet another example, the ground-truth prediction for a particular patient predictive data entity may describe whether genetic tests for the particular patient predictive data entity depict a genetic propensity for a particular condition such as NSCLC. As described above, as only a segment of a plurality of predictive data entities may be associated with a ground-truth prediction (e.g., only a segment of the patient population may have a confirmed diagnosis/condition/test result), the segment of the plurality of predictive data entities that is associated with a ground-truth prediction is distinctively referred to herein as the labeled segment of the plurality of predictive data entities.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

FIG. 1 is a schematic diagram of an example system architecture 100 for performing predictive data analysis steps/operations and generating corresponding user interface data (e.g., for providing and/or updating a user interface). The system architecture 100 includes a predictive data analysis system 101 comprising a predictive data analysis computing entity 106 configured to generate predictive outputs that lead to performing one or more prediction-based actions. The predictive data analysis system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The system architecture 100 includes a storage subsystem 108 configured to store at least a portion of the data utilized by the predictive data analysis system 101. The predictive data analysis computing entity 106 may be in communication with one or more external computing entities 102. The predictive data analysis computing entity 106 may be configured to receive requests and/or data from external computing entities 102, process the requests and/or data to generate predictive outputs (e.g., predictive data analysis data objects), and provide the predictive outputs to the external computing entities 102. The external computing entity 102 (e.g., management computing entity) may periodically update/provide raw input data (e.g., data objects describing primary events and/or secondary events) to the predictive data analysis system 101. The external computing entities 102 may further generate user interface data (e.g., one or more data objects) corresponding to the predictive outputs and may provide (e.g., transmit, send and/or the like) the user interface data corresponding with the predictive outputs for presentation to user computing entities operated by end-users.

The storage subsystem 108 may be configured to store at least a portion of the data utilized by the predictive data analysis computing entity 106 to perform predictive data analysis steps/operations and tasks. The storage subsystem 108 may be configured to store at least a portion of operational data and/or operational configuration data including operational instructions and parameters utilized by the predictive data analysis computing entity 106 to perform predictive data analysis steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

A. Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include, or be in communication with, a processing element 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include, or be in communication with, non-volatile media (also referred to as non-volatile storage, memory, memory storage, memory circuitry and/or similar terms used herein interchangeably). In one embodiment, the non-volatile storage or memory may include non-volatile memory 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include, or be in communication with, volatile media (also referred to as volatile storage, memory, memory storage, memory circuitry and/or similar terms used herein interchangeably). In one embodiment, the volatile storage or memory may also include volatile memory 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include a communications interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include, or be in communication with, one or more input elements, such as a keyboard input, a mouse input, a touch screen/display input, motion input, movement input, audio input, pointing device input, joystick input, keypad input, and/or the like. The predictive data analysis computing entity 106 may also include, or be in communication with, one or more output elements (not shown), such as audio output, video output, screen/display output, motion output, movement output, and/or the like.

B. Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein.

External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

IV. Exemplary System Operations

Various embodiments of the present invention disclose techniques for performing predictive prioritization that utilize the combination of a supervised trained machine learning model and an unsupervised trained machine learning model to infer relationships between key target features that are estimated to be highly descriptive of optimal prioritization of predictive data entities. These inferred relationships are then used in some embodiments to generate computationally inefficient prioritization machine learning models that are able to efficiently and reliably predict optimal prioritization schemes for predictive data entities. Two of the key technical advantages of the noted techniques relate to: (i) the efficiency advantage resulting from eliminating the need for using the supervised trained machine learning model and the unsupervised trained machine learning model post training, and (ii) the reliability advantage resulting from using both supervised learning and unsupervised learning to learn cross-feature relationships and feature refinements, which in turn enables learning predictive patterns even when using small amounts of labeled training data.

FIG. 4 is a flowchart diagram of an example process 400 for hybrid predictive prioritization of a plurality of predictive data entities. Via the various steps/operations of the process 400, the predictive data analysis computing entity 106 can combine supervised machine learning techniques and unsupervised machine learning techniques to generate one or more selected features characterizing a prioritization machine learning model, where the prioritization machine learning model can be used to generate predicted prioritization scores for the plurality of predictive data entities in an efficient and reliable manner.

The process 400 begins at step/operation 401 when the predictive data analysis computing entity 106 identifies a predictive entity data object for each predictive data entity of the plurality of predictive data entities. For example, the predictive data analysis computing entity 106 may generate the predictive entity data object for a patient predictive data entity by combining electronic medical record (EMR) for the patient predictive data entity, demographic data for the patient predictive data entity, activity data for the patient predictive data entity, and/or the like.

In general, a predictive data entity may describe a real-world entity and/or a virtual entity about which one or more predictive data analysis inferences are generated using a hybrid predictive prioritization process. For example, a predictive data entity may describe a patient predictive data entity whose corresponding patient predictive entity data object is processed using a hybrid predictive prioritization process in order to generate at least one of the following predictive data analysis inferences: (i) one or more predicted prioritization scores that each describe an inferred relative significance of administering a corresponding genetic test for a corresponding medical condition to the patient associated with the patient predictive data entity, and (ii) a predicted recommended ordering of each genetic test that is deemed applicable/recommended for the patient associated with the patient predictive data entity based at least in part on each predicted prioritization score associated with the patient predictive data entity.

Moreover, a predictive entity data object may describe one or more data fields associated with a corresponding predictive data entity, where the one or more data fields may be processed by a predictive prioritization process in order to generate one or more predictive data analysis inferences for the corresponding predictive data entity. For example, given a predictive data entity that describes a patient predictive data entity, the predictive entity data object for the patient predictive data entity may describe one or more data fields associated with the patient predictive data entity that are processed using a predictive prioritization process in order to generate at least one of the following predictive data analysis inferences: (i) one or more predicted prioritization scores that each describe an inferred relative significance of administering a corresponding genetic test for a corresponding medical condition to the patient associated with the patient predictive data entity, and (ii) a predicted recommended ordering of each genetic test that is deemed applicable/recommended for the patient associated with the patient predictive data entity based at least in part on each predicted prioritization score associated with the patient predictive data entity. In the noted example, the predictive entity data object may describe at least one of the following: EMR data associated with the patient predictive data entity, medical claim data associated with the patient predictive data entity, prescription history data associated with the patient predictive data entity, medical history data associated with the patient predictive data entity, demographic profile data associated with the patient predictive data entity, socio-economic profile data associated with the patient predictive data entity, activity recording data associated with the patient predictive data entity (such as activity recording data associated with associated with the patient predictive data entity that are captured using one or more activity recording wearable devices associated with the patient predictive data entity), family medical history data associated with the patient predictive data entity, blood test result data associated with the patient predictive data entity, diagnosis data associated with the patient predictive data entity, biomarker data associated with the patient predictive data entity, medication history data associated with the patient predictive data entity, comorbidity data associated with the patient predictive data entity, glucometer data associated with the patient predictive data entity (such as glucometer data recorded using a glucometer device such as a Medtronic Guardian Connect System device associated with the patient predictive data entity), medical cohort characterization data associated with the patient predictive data entity, medical note data associated with the patient predictive data entity, medical imaging data associated with the predictive data entity, clinical data associated with the patient predictive data entity, data describing correspondence of the patient associated with the patient predictive data entity with one or more observed/recorded/preconfigured medical patterns (e.g., data describing that the patient associated with the patient predictive data entity is a male patient between 18 and 75 inclusive and that the male patients between the noted age range have a higher likelihood of non-small cell lung cancer), and/or the like.

At step/operation 402, the predictive data analysis computing entity 106 performs one or more feature engineering operations on the predictive entity data objects to generate a feature data object for each predictive data entity. In some embodiments, the predictive data analysis computing entity 106 processes each predictive entity data object for a particular predictive data entity using the one or more feature engineering operations to generate the feature data object for the predictive data entity.

In some embodiments, in relation to generating a particular feature data object based at least in part on a particular predictive entity data object, step/operation 402 may be performed in accordance with the process depicted in FIG. 5. The process depicted in FIG. 5 begins at step/operation 501 when the predictive data analysis computing entity 106 determines one or more format-specific input data groupings for the particular predictive entity data object. A format-specific input data grouping may describe a subset of the input data described by a corresponding predictive entity data object that has a particular data modeling format and/or data type format. For example, the predictive entity data object for a particular patient predictive data entity may be divided into the following format-specific input data groupings: a first format-specific input data grouping that includes image data (e.g., medical image data) associated with the patient predictive data entity, a second format-specific input data grouping that describes unstructured data (e.g., clinical note data, medical note data, patient medical journal data, and/or the like) associated with the patient predictive data entity, a third format-specific input data grouping that describes structured data (e.g., blood test report data, activity recording data, diagnosis data, prescription history data, and/or the like) associated with the patient predictive data entity, and a fourth format-specific input data grouping that describes non-physiological and/or supplemental data (e.g., demographic profile data, socioeconomic profile data, and/or the like) associated with the patient predictive data entity. In some embodiments, one objective of dividing input data associated with a predictive entity data object into format-specific input data groupings is to facilitate integration of external feedback data into each format-specific input data grouping by directing each format-specific input data grouping to external feedback agents (e.g., subject matter expert (SME) agents) that are deemed to have particular expertise/background in matters pertaining to the format-specific input data grouping.

At step/operation 502, the predictive data analysis computing entity 106 integrates external feedback data (e.g., SME data) into each format-specific input data grouping to generate an updated format-specific input data grouping. In some embodiments, to integrate external feedback data (e.g., SME data) into a format-specific input data grouping, the predictive data analysis computing entity 106 provides the format-specific input data grouping to an external feedback agent, receives refinement/amendment data from the external feedback agent, and integrates the refinement/amendment data to the format-specific input data grouping. Examples of external feedback agents include clinical experts, such as medical imaging experts, medical note experts, demographic profile experts, and/or the like. In some embodiments, the external feedback data for a corresponding format-specific input data grouping is configured to highlight deficiencies, omissions, and/or errors in the corresponding format-specific input data grouping, and the predictive data analysis computing entity 106 is configured to refine/amend the corresponding format-specific input data grouping by adding omitted features into the format-specific input data grouping as well as removing or replacing deficient/error-prone features from the format-specific input data grouping.

At step/operation 503, the predictive data analysis computing entity 106 performs an initial pattern recognition traversal of each updated format-specific input data grouping to detect a set of initial features for the updated format-specific input data grouping. In some embodiments, to perform the initial pattern recognition traversal of an updated format-specific input data grouping to detect the set of initial features for the updated format-specific input data grouping, the predictive data analysis computing entity 106 searches the updated format-specific input data grouping to detect whether the updated format-specific input data grouping describes one or more data patterns that are deemed correlated with a target medical condition. For example, to detect whether an updated format-specific input data grouping describes known risk factors associated with the tumor expressing PD-L1, the predictive data analysis computing entity 106 may detect whether the updated format-specific input data grouping describes that a corresponding patient predictive data entity is associated with at least one of the following: epidermal growth factor receptor (EGFR) mutations in lung adenocarcinomas, elevated spirometry, persistent cough, above-65 age, and/or the like.

In some embodiments, to perform an initial pattern recognition traversal of an image-based updated format-specific input data grouping to detect a set of initial features for the image-based updated format-specific input data grouping, the predictive data analysis computing entity 106 performs one or more image processing operations (e.g., using a convolutional neural network) on the image-based updated format-specific input data grouping to determine whether the output of the one or more image processing operations describes that the image-based updated format-specific input data grouping is indicative of one or more data patterns that are deemed correlated to a target predictive condition (e.g., a target medical condition). In some embodiments, to perform an initial pattern recognition traversal of an image-based updated format-specific input data grouping to detect a set of initial features for the image-based updated format-specific input data grouping, the predictive data analysis computing entity 106 processes image metadata associated with the image-based updated format-specific input data grouping (e.g., using a fully connected feed-forward neural network) to determine whether the output of the one or more processing the image metadata describes that the image-based updated format-specific input data grouping is indicative of one or more data patterns that are deemed correlated to a target predictive condition (e.g., a target medical condition).

In some embodiments, to perform an initial pattern recognition traversal of a structured updated format-specific input data grouping to detect a set of initial features for the structured updated format-specific input data grouping, the predictive data analysis computing entity 106 performs one or more structured data processing operations (e.g., using a fully connected feed-forward neural network) on the structured updated format-specific input data grouping to determine whether the output of the one or more structured data processing operations describes that the structured updated format-specific input data grouping is indicative of one or more data patterns that are deemed correlated to a target predictive condition (e.g., a target medical condition). In some embodiments, to perform an initial pattern recognition traversal of a structured updated format-specific input data grouping to detect a set of initial features for the image-based updated format-specific input data grouping, the predictive data analysis computing entity 106 processes structured metadata associated with the structured updated format-specific input data grouping (e.g., using a fully connected feed-forward neural network) to determine whether the output of the one or more processing the structured metadata describes that the structured updated format-specific input data grouping is indicative of one or more data patterns that are deemed correlated to a target predictive condition (e.g., a target medical condition).

In some embodiments, to perform an initial pattern recognition traversal of an unstructured updated format-specific input data grouping to detect a set of initial features for the unstructured updated format-specific input data grouping, the predictive data analysis computing entity 106 performs one or more structured data processing operations (e.g., using a recurrent neural network) on the unstructured updated format-specific input data grouping to determine whether the output of the one or more structured data processing operations describes that the unstructured updated format-specific input data grouping is indicative of one or more data patterns that are deemed correlated to a target predictive condition (e.g., a target medical condition). In some embodiments, to perform an initial pattern recognition traversal of an unstructured updated format-specific input data grouping to detect a set of initial features for the unstructured updated format-specific input data grouping, the predictive data analysis computing entity 106 processes unstructured metadata associated with the unstructured updated format-specific input data grouping (e.g., using a fully connected feed-forward neural network) to determine whether the output of the one or more processing the unstructured metadata describes that the structured updated format-specific input data grouping is indicative of one or more data patterns that are deemed correlated to a target predictive condition (e.g., a target medical condition).

At step/operation 504, the predictive data analysis computing entity 106 performs one or more explanatory data analysis operations on the updated format-specific input data groupings using the set of initial features to generate one or more updated features for the particular predictive entity data object. In some embodiments, to perform the one or more explanatory data analysis operations on the updated format-specific input data groupings to generate one or more updated features for the particular predictive entity data object, the predictive data analysis computing entity 106 performs the following operations: (i) for each initial feature in the set of initial features for an updated format-specific input data grouping, generating a numerical representation value such as a one-hot-coding categorical variable representation with respect to the updated format-specific input data grouping, (ii) processing the numerical representation values for the initial features across all of the plurality of predictive data entities using a cross-feature collinearity detection model to detect co-linearities across the numerical representations and consolidate the set of initial features to reduce cross-feature co-linearities, and (iii) processing the numerical representation values for the consolidated features across all of the plurality of predictive data entities using a feature deficiency detection machine learning model to detect defective features having an above-threshold count/ratio of missing values and removing the defective features from the consolidated features to generate the updated features.

For example, consider a set of initial features that includes features $F_1$, $F_2$, $F_3$, and $F_4$. By processing numerical representations for the set of initial features across all of the plurality of predictive data entities using a cross-feature collinearity detection model, the predictive data analysis computing entity 106 may first determine that the features $F_1$ and $F_2$ are co-linear. To address this cross-feature co-linearity, the predictive data analysis computing entity 106 may remove $F_1$ from the set of initial features to generate a set of consolidated features that includes $F_2$, $F_3$, and $F_4$. Afterward, the predictive data analysis computing entity 106 may process the numerical representation values for the consolidated features across all of the plurality of predictive data entities using a feature deficiency detection machine learning model to detect that $F_4$ has an above-threshold count/ratio of missing values. To address this feature value deficiency, the predictive data analysis computing entity 106 may remove $F_4$ from the set of initial features to generate a set of updated features that includes $F_2$ and $F_3$.

As another example, consider a set of initial features that includes features $F_1$, $F_2$, $F_3$, and $F_4$. By processing numerical representations for the set of initial features across all of the plurality of predictive data entities using a cross-feature collinearity detection model, the predictive data analysis computing entity 106 may first determine that the features $F_1$ and $F_2$ are co-linear. To address this cross-feature co-linearity, the predictive data analysis computing entity 106 may replace the features $F_1$ and $F_2$ from the set of initial features with a merged feature $F_5$ to generate a set of consolidated features that includes $F_2$, $F_3$, $F_4$, and $F_5$. Afterward, the predictive data analysis computing entity 106 may process the numerical representation values for the consolidated features across all of the plurality of predictive data entities using a feature deficiency detection machine learning model to detect that $F_4$ has an above-threshold count/ratio of missing values. To address this feature value deficiency, the predictive data analysis computing entity 106 may remove $F_4$ from the set of initial features to generate a set of updated features that includes $F_2$, $F_3$, and $F_5$.

In some embodiments, to perform the one or more explanatory data analysis operations on the updated format-specific input data groupings to generate one or more updated features for the particular predictive entity data object, the predictive data analysis computing entity 106 performs the following operations: (i) for each initial feature in the set of initial features for an updated format-specific input data grouping, generating a numerical representation value such as a one-hot-coding categorical variable representation with respect to the updated format-specific input data grouping, (ii) processing the numerical representation values for the initial features across all of the plurality of predictive data entities using a feature deficiency detection machine learning model to detect defective features having an above-threshold count/ratio of missing values and removing the defective features from the initial features to generate deficiency-removed features, and (iii) processing the numerical representation values for the deficiency-removed features across all of the plurality of predictive data entities using a cross-feature collinearity detection model to detect co-linearities across the numerical representations and consolidate the deficiency-removed set of features to reduce cross-feature co-linearities and generate updated features.

For example, consider a set of initial features that includes features $F_1$, $F_2$, $F_3$, and $F_4$. By processing the numerical representation values for the initial features across all of the plurality of predictive data entities using a feature deficiency detection machine learning model, the predictive data analysis computing entity 106 may determine that $F_4$ has an above-threshold count/ratio of missing values. To address this feature value deficiency, the predictive data analysis computing entity 106 may remove $F_4$ from the set of initial features to generate a set of deficiency-removed features that includes $F_1$, $F_2$, and $F_3$. Afterward, the predictive data analysis computing entity 106 may process the numerical representations for the deficiency-removed set of features across all of the plurality of predictive data entities using a cross-feature collinearity detection model to determine that the features $F_1$ and $F_2$ are co-linear. To address this cross-feature co-linearity, the predictive data analysis computing entity 106 may remove $F_1$ from the set of initial features to generate a set of consolidated features that includes $F_2$, and $F_3$.

As another example, consider a set of initial features that includes features $F_1$, $F_2$, $F_3$, and $F_4$. By processing the numerical representation values for the initial features across all of the plurality of predictive data entities using a feature deficiency detection machine learning model, the predictive data analysis computing entity 106 may determine that $F_4$ has an above-threshold count/ratio of missing values. To address this feature value deficiency, the predictive data analysis computing entity 106 may remove $F_4$ from the set of initial features to generate a set of deficiency-removed features that includes $F_1$, $F_2$, and $F_3$. Afterward, the predictive data analysis computing entity 106 may process the numerical representations for the deficiency-removed set of features across all of the plurality of predictive data entities using a cross-feature collinearity detection model to determine that the features $F_1$ and $F_2$ are co-linear. To address this cross-feature co-linearity, the predictive data analysis computing entity 106 may replace the features $F_1$ and $F_2$ from the set of initial features with a merged feature $F_5$ to generate a set of consolidated features that includes $F_3$ and $F_5$.

At step/operation 505, the predictive data analysis computing entity 106 generates the particular feature data object based at least in part on the updated features. In some embodiments, the predictive data analysis computing entity 106 generates an updated feature value for each updated feature in relation to the particular predictive data entity and combines the updated features values to generate the feature data object for the particular predictive entity data object.

In some embodiments, the feature data object describes the feature values associated with a predictive data entity that are inferred based at least in part on the predictive entity data object for the predictive data entity and that may be used to train a supervised machine learning model (e.g., a multi-input-type supervised machine learning model) that is configured to detect a likelihood of presence of a target predictive condition (e.g., a target medical condition) with respect to the predictive entity. In some embodiments, the feature data object includes an updated feature value for each updated value, where the updated feature value describes the extent to which the predictive entity data object associated with the feature data object describes a data pattern associated with the corresponding updated feature that is associated with the updated feature. For example, an exemplary feature data object may describe a one-hot-encoding feature value for each updated feature. In some embodiments, the feature data object for a corresponding predictive entity data object that is in turn associated with a corresponding predictive data entity includes at least one of the following: (i) feature values associated with one or more features whose missing value count/ratio fails to exceed a missing value threshold value, (ii) image data in the corresponding predictive entity data object (which may for example be supplied as an input to an image processing model, such as a depth-wise searchable convolutional neural network model), and/or image metadata inferred based at least in part on image data in the corresponding predictive entity data object, (iii) unstructured data in the corresponding predictive entity data object that may be used to generate features that may be supplied as an input to a recurrent neural network, and (iv) other features values related to features deemed important based at least in part on the results of data engineering operations and/or based at least in part on external data such as SME data. In some embodiments, the feature data object may include various per-model segments that each is configured to be supplied as an input to a different per-input-type component of a multi-input-type supervised machine learning model. For example, the feature data object may include an image-based segment that is configured to be supplied to an image processing component of a multi-input-type supervised machine learning model, such as an image processing component that includes an image processing model, e.g., a depth-wise searchable convolutional neural network model. As another example, the feature data object may include an unstructured segment that is configured to be supplied to an unstructured data processing component of a multi-input-type supervised machine learning model, such as an unstructured data processing component that includes an unstructured data processing model, e.g., a recurrent neural network including a Long Short Term Memory (LSTM) RNN. As yet another example, the feature data object may include a structured segment that is configured to be supplied to a structured data processing component of a multi-input-type supervised machine learning model, such as a structured data processing component that includes an structured data processing model, e.g., a fully connected feedforward neural network.

Returning to FIG. 4, at step/operation 403, the predictive data analysis computing entity 106 trains a refined multi-input-type supervised machine learning model based at least in part on each feature data object for a labeled segment of the plurality of predictive data entities. However, while various embodiments of the present invention describe training a multi-input-type supervised machine learning model, a person of ordinary skill in the relevant technology will recognize that various inventive techniques disclosed herein may be implemented using a single-input-type machine learning model.

In some embodiments, step/operation 403 may be performed in accordance with the process depicted in FIG. 6. The process depicted in FIG. 6 begins at step/operation 601 when the predictive data analysis computing entity 106 identifies a labeled segment of the plurality of predictive data entities which includes a subset of the plurality of predictive data entities that have a ground-truth prediction associated with them. A ground-truth prediction may describe an observed/recorded label associated with a corresponding predictive data entity that describes whether the predictive data entity is deemed to associated with a target predictive condition for the ground-truth prediction. For example, the ground-truth prediction for a particular patient predictive data entity may describe whether the particular patient predictive data entity has been observed/recorded to have a particular diagnosis, such as a diagnosis for non-small-cell lung carcinoma (NSCLC). As another example, the ground-truth prediction for a particular patient predictive data entity may describe whether the particular patient predictive data entity has been observed/recorded to have been tested positive for a particular condition such as NSCLC. As yet another example, the ground-truth prediction for a particular patient predictive data entity may describe whether genetic tests for the particular patient predictive data entity depict a genetic propensity for a particular condition such as NSCLC. As described above, as only a segment of a plurality of predictive data entities may be associated with a ground-truth prediction (e.g., only a segment of the patient population may have a confirmed diagnosis/condition/test result), the segment of the plurality of predictive data entities that is associated with a ground-truth prediction is distinctively referred to herein as the labeled segment of the plurality of predictive data entities.

At step/operation 602, the predictive data analysis computing entity 106 trains one or more initial multi-input-type supervised machine learning models based at least in part on each feature data object for a predictive data entity in the labeled segment and the ground-truth prediction for the feature data object. In some embodiments, to train the initial candidate trained multi-input machine learning models, the predictive data analysis computing entity 106 performs the following operations: (i) performing an initial set of cross-validation operations (e.g., an initial set of k-fold cross-validation operations) on the feature data objects for the predictive entity data objects in the labeled segment to detect a plurality of feature segments of the feature data objects for the predictive entity data objects in the labeled segment, (ii) train an initial multi-input-type supervised machine learning model using a corresponding feature segment of the feature data objects and the ground-truth predictions for the feature segment, (iii) test the initial multi-input-type supervised machine learning model using the feature data objects outside the corresponding feature segment for the initial multi-input-type supervised machine learning model to detect whether the initial multi-input-type supervised machine learning models is insufficiently accurate and/or overfitted, and (iv) remove an initial multi-input-type supervised machine learning model from the initial multi-input-type supervised machine learning models if the initial multi-input-type supervised machine learning model is deemed to be insufficiently accurate and/or overfitted.

For example, consider a labeled segment of the predictive data entities P1-P12 that are associated with feature data objects F1-F12 and ground-truth predictions G1-G12 respectively. In an exemplary embodiment, to generate initial multi-input-type supervised machine learning models based at least in part on the feature data objects F1-F12, the predictive data analysis computing entity 106 first performs cross-validation to divide the feature data objects F1-F12 into a first feature segment S1={F1, F2, F3, F4}, a second feature segment S2={F5, F6, F7, F8}, and a third feature segment S3={F9, F10, F11, and F12}. Afterward, the predictive data analysis computing entity 106 trains three initial multi-input-type supervised machine learning models: a first initial multi-input-type supervised machine learning model M1 based at least in part on S1 and G1-G4, a second initial multi-input-type supervised machine learning model M2 based at least in part on S2 and G5-G8, and a third initial multi-input-type supervised machine learning model M3 based at least in part on S3 and G9-G12. Thereafter, the predictive data analysis computing entity 106 tests M1 based at least in part on S2 and S3 as well as G5-G12 to determine whether M2 is insufficiently accurate and/or overfitted, tests M2 based at least in part on S1 and S3 as well as G1-G4 and G9-G12 to determine whether M2 is insufficiently accurate and/or overfitted, and tests M3 based at least in part on S1 and S2 as well as G1-G8 to determine whether M3 is insufficiently accurate and/or overfitted. Suppose that as a result of the noted testing operations the predictive data analysis computing entity 106 determines that M1 and M2 are sufficiently accurate and not overfitted, while M3 is insufficiently accurate and/or overfitted. Given this, the predictive data analysis computing entity 106 may determine that the initial multi-input-type supervised machine learning models include M1 and M2.

At step/operation 603, the predictive data analysis computing entity 106 generates refined feature data objects each characterized by a set of refined features by processing the feature data objects using one or more feature selection operations (e.g., one or more principal component analysis operations) in light of the classification accuracy of the initial multi-input-type supervised machine learning models. For example, the predictive data analysis computing entity 106 may identify particular features associated with the feature data objects that have a below-threshold contribution to the classification accuracy of the initial multi-input-type supervised machine learning models and remove the particular features from the refined features characterizing the refined feature data objects. As another example, the predictive data analysis computing entity 106 may merge two or more particular features associated with the feature data objects that have a below-threshold contribution to the classification accuracy of the initial multi-input-type supervised machine learning models into a merged feature that has an above-threshold contribution to the classification accuracy of the initial multi-input-type supervised machine learning models, and then may include the merged feature as one of the refined features characterizing the refined feature data objects.

At step/operation 604, the predictive data analysis computing entity 106 generates one or more model-related feature data objects that are characterized by a set of model-related features that include each model-related feature subset for an initial multi-input-type supervised machine learning model of the one or more initial multi-input-type supervised machine learning models. To do so, the predictive data analysis computing entity 106 may first determine a model-related feature subset of the refined features for an initial multi-input-type supervised machine learning model that describes a subset of the refined features that is deemed to have significant predictive correlation with the initial multi-input-type supervised machine learning model. For example, the predictive data analysis computing entity 106 may determine, for each feature-model pair that is associated with a refined feature and an initial multi-input-type supervised machine learning model, a predictive contribution estimate that describes an estimated predictive contribution of the refined feature to the initial multi-input-type supervised machine learning model. Afterward, the predictive data analysis computing entity 106 selects the model-related feature subset of the refined features for a particular initial multi-input-type supervised machine learning model based at least in part on each predictive contribution estimate for a feature-model pair that includes the particular trained multi-input-type supervised machine learning model. In some embodiments, the predictive significance estimate for a particular feature-model pair is determined based at least in part on a minimum-redundancy-maximum-relevancy measure (mRMR), such as mRMR measures described in Peng et al., *Feature Selection Based at least in part on Mutual Information Criteria of Max-Dependency, Max-Relevance, and Min-Redundancy* (2005), available online at https://ieeexplore.ieee.org/document/1453511. In some embodiments, step/operation 604 may be performed in accordance with the techniques described in Sickit Learn, 1.13 *Feature Selection* (accessed on Oct. 6, 2020), available online at https://scikit-learn.org/stable/modules/feature_selection.html.

For example, the predictive data analysis computing entity 106 may determine that a refined feature is in the model-related feature subset for a trained multi-input-type supervised machine learning model if the predictive significance estimate for a feature-model pair that is associated with the refined feature and the trained multi-input-type supervised machine learning model exceeds a predictive significance estimate threshold. As another example, the predictive data analysis computing entity 106 may determine that a refined feature is in the model-related feature subset for a trained multi-input-type supervised machine learning model if the predictive significance estimate for a feature-model pair that is associated with the refined feature and the trained multi-input-type supervised machine learning model is among the top n predictive significance estimates for all predictive significance estimates for feature-model pairs that are associated with the trained multi-input-type supervised machine learning model, where n may be a hyper-parameter of the predictive data analysis computing entity 106.

At step/operation 605, the predictive data analysis computing entity 106 generates an updated multi-input-type supervised machine learning model based at least in part on the model-related feature data objects. In some embodiments, to generate the updated multi-input-type supervised machine learning model, the predictive data analysis computing entity 106 performs one or more follow-up cross-validation operations (e.g., one or more follow-up k-fold cross-validation operations) on the model-related feature data objects to generate a model-related feature segment of the model-related feature data objects and uses the model-related feature segment and the ground-truth predictions for the model-related feature segment to generate the update candidate trained multi-input-type supervised machine learning model in accordance with techniques similar to the techniques described above in relation to step/operation 602.

At step/operation 606, the predictive data analysis computing entity 106 generates one or more model testing outputs for the updated multi-input-type supervised machine learning model by testing the updated multi-input-type supervised machine learning model based at least in part on those related data objects that fall outside the corresponding feature segment for the updated multi-input-type supervised machine learning model. A model testing output generated herein may describe an estimated degree of accuracy of a corresponding updated multi-input-type supervised machine learning model, where the model testing output may be determined based at least in part on testing results for the updated multi-input-type supervised machine learning model generated via processing the related data objects that fall outside the corresponding feature segment for the updated multi-input-type supervised machine learning model to generate testing predictions and comparing the testing predictions to ground-truth predictions for the related data objects that fall outside the corresponding feature segment for the updated multi-input-type supervised machine learning model. An example of a model testing output is an area under the receiver operating characteristic curve (AUC) measure.

At step/operation 607, the predictive data analysis computing entity 106 performs one or more hyper-parameter tuning operations for the updated multi-input-type supervised machine learning model based at least in part on the model testing outputs for the updated multi-input-type supervised machine learning model. For example, the predictive data analysis computing entity 106 may select a set of hyper-parameters for the updated multi-input-type supervised machine learning model that optimizes one or more model testing outputs for the updated multi-input-type supervised machine learning model, e.g., an AUC measure for the updated multi-input-type supervised machine learning model.

At step/operation 608, the predictive data analysis computing entity 106 determines whether an accuracy metric (e.g., an AUC measure) for the updated multi-input-type supervised machine learning model is an optimal accuracy metric (e.g., is an above-threshold accuracy metric, is the best possible accuracy metric, and/or the like). If the predictive data analysis computing entity 106 determines that the accuracy metric (e.g., the AUC measure) for the updated multi-input-type supervised machine learning model is not an optimal accuracy metric, the predictive data analysis computing entity 106 returns to step/operation 603 to further refine feature data objects and use the further-refined feature data objects to generate a new updated multi-input-type supervised machine learning model that is then trained and tested.

However, if the predictive data analysis computing entity 106 determines that the accuracy metric (e.g., the AUC measure) for the updated multi-input-type supervised machine learning model is an optimal accuracy metric, the predictive data analysis computing entity 106 proceeds to step/operation 609 to generate the refined multi-input-type supervised machine learning model based at least in part on the updated multi-input-type supervised machine learning model. In some embodiments, to generate the refined multi-input-type supervised machine learning model based at least in part on the updated multi-input-type supervised machine learning model, the predictive data analysis computing entity 106 determines whether external data (e.g., genetic test result data, such as National Center for Biotechnology Information Gene data) indicate that a particular refined feature is associated with the target predictive condition of the updated multi-input-type supervised machine learning model, and if so ensures that the particular refined feature is associated with an above-threshold (e.g., an above-one) weight/parameter according to the refined multi-input-type supervised machine learning model. For example, the predictive data analysis computing entity 106 may determine whether external data (e.g., genetic test result data, such as National Center for Biotechnology Information Gene data) indicate that a particular refined feature is associated with a gene/genetic pattern that is in turn correlated with the target predictive condition of the updated multi-input-type supervised machine learning model, and if so ensures that the particular refined feature is associated with an above-threshold (e.g., an above-one) weight/parameter according to the refined multi-input-type supervised machine learning model.

Returning to FIG. 4, at step/operation 404, the predictive data analysis computing entity 106 determines one or more target features based at least in part on the refined features associated with the refined multi-input-type supervised machine learning model. In some embodiments, to determine the target features, the predictive data analysis computing entity 106 first maps each predictive data entity of the plurality of predictive data entity to a multi-dimensional unsupervised machine learning space, where each dimension of the multi-dimensional unsupervised machine learning space is characterized by a refined feature of the refined features associated with the refined multi-input-type supervised machine learning model. Afterward, the predictive data analysis computing entity 106 applies one or more clustering techniques (e.g., ordering points to identify the clustering structure (OPTICS), density-based spatial clustering of applications with noise (DBSCAN), and/or the like) to identify one or more target entity clusters of the mappings of the predictive data entities, where each target entity cluster comprises at least one mapping of a predictive data entity that is in a positive-labeled subset of the plurality of predictive data entities. Thereafter, the predictive data analysis computing entity 106 determines (e.g., using a Dunn's index measure), for each refined feature of the one or more refined features, a degree of correlation of the refined feature across the target entity clusters. Afterward, the predictive data analysis computing entity 106 selects the target features based at least in part on a subset of the refined features having an above-threshold degree of correlation and/or a subset of the refined features comprising the refined features with top m degrees of correlation as the set of target features, where m may be a hyper-parameter of the predictive data analysis computing entity 106.

In some embodiments, step/operation 404 may be performed in accordance with the process that is depicted in FIG. 7. The process that is depicted in FIG. 7 begins at step/operation 701 begins at step/operation 701 when predictive data analysis computing entity 106 generates the multi-dimensional unsupervised machine learning space. As described above, the multi-dimensional unsupervised machine learning space includes a mapping for each predictive data entity based at least in part on the refined feature values for the predictive data entity. An operational example of a multi-dimensional unsupervised machine learning space 800 characterized by two refined features 801-802 is depicted in FIG. 8. As depicted in FIG. 8, the multi-dimensional unsupervised machine learning space 800 includes mappings for five predictive data entities 811-815, where the predictive data entities 811-812 have a positive ground-truth prediction.

At step/operation 702, the predictive data analysis computing entity 106 determines target entity clusters based at least in part on the multi-dimensional unsupervised machine learning space. Each target entity cluster includes a group of predictive data entities that are deemed sufficiently proximate to at least one positive-labeled predictive data entity according to a proximity metric (e.g., a Euclidean proximity metric, a Manhattan proximity metric, and/or the like) defined for the multi-dimensional unsupervised machine learning space. For example, as depicted in FIG. 8, two target entity clusters are determined: a first target entity cluster 821 that includes the positive-labeled predictive data entity 811 and the predictive data entity 813, and a second target entity cluster 822 that includes the positive-labeled predictive data entity 812 and the predictive data entity 814.

At step/operation 703, the predictive data analysis computing entity 106 determines a measure of correlation for each refined feature across the target entity clusters. In some embodiments, to determine the measure of correlation for a refined feature, the predictive data analysis computing entity 106 determines a per-cluster measure of correlation for the refined feature across the mappings in each target entity cluster, and then selects the per-cluster measure of correlation having the highest value as the measure of correlation for the refined feature. In some embodiments, to determine the measure of correlation for a refined feature, the predictive data analysis computing entity 106 determines a per-cluster measure of correlation for the refined feature across the mappings in each target entity cluster, and then determines an average of each per-cluster measure of correlation for the refined feature as the measure of correlation for the refined feature.

At step/operation 704, the predictive data analysis computing entity 106 determines the target features based at least in part on each measure of correlation for a refined feature. In some embodiments, the predictive data analysis computing entity 106 selects the target features based at least in part on a subset of the refined features having an above-threshold degree of correlation as the target features. In some embodiments, the predictive data analysis computing entity 106 selects the target features based at least in part on a subset of the refined features comprising the refined features with top m degrees of correlation as the set of target features, where m may be a hyper-parameter of the predictive data analysis computing entity 106.

Returning to FIG. 4, at step/operation 405, the predictive data analysis computing entity 106 generates a prioritization machine learning model based at least in part on the target features. The prioritization machine learning model may be a machine learning model that is configured to apply a linear or a non-linear combination of the target feature values for a predictive data entity to determine a predicted prioritization score for the predictive data entity. In some embodiments, the prioritization machine learning model defines a parameter value for each target feature, where the initial value of the parameter for the target feature may be set to a default value or to a value determined based at least in part on the measure of correlation of the target feature as determined using the target entity clusters inferred from the multi-dimensional unsupervised machine learning space, as described above. In some embodiments, where the predicted prioritization scores are used to recommend genetic testing operations for patients associated with the predictive data entities, the test results are used to set the values of the parameters of the target features using one or more training algorithms and/or one or more parameter value optimization algorithms, such as using gradient descent.

At step/operation 406, the predictive data analysis computing entity 106 performs one or more prediction-based actions using the prioritization machine learning model. In some embodiments, the predictive data analysis computing entity 106 processes the target feature values of each predictive data entity using the prioritization machine learning model in order to generate a predicted prioritization score for each predictive data entity. Thereafter, the predictive data analysis computing entity 106 selects as prioritized predictive data entities a target subset of the predictive data entities having the k highest predicted prioritization scores, where k may be a hyper-parameter of the predictive data analysis computing entity 106, such as a hyper-parameter defining a number of available genetic tests. In some embodiments, the predictive data analysis computing entity 106 performs the prediction-based actions based at least in part on the target subset.

For example, in some embodiments, the predictive data analysis computing entity 106 determines that each patient associated with the target subset of the patient predictive data entities should be administered a genetic test associated with the prioritization machine learning model. Afterward, the predictive data analysis computing entity 106 may use clinical data about priority and/or clinical utility of the genetic tests assigned to each patient predictive data entity to determine an ordering of genetic tests administered to the noted genetic tests. Thereafter, the predictive data analysis computing entity 106 performs one or more prediction-based actions based at least in part on the genetic test assignments and/or genetic test orderings. For example, the predictive data analysis computing entity 106 may generate a prediction output user interface that describes genetic test assignments and/or genetic testing orderings for one or more patient predictive data entities. An operational example of such a prediction output user interface 900 is depicted in FIG. 9. As depicted in FIG. 9, the patient "John Smith" is recommended to undergo the following order of recommended genetic tests: the genetic test pertaining to lung cancer, followed by the genetic test pertaining to Huntington's disease, followed by the genetic test pertaining to cystic fibrosis.

V. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for predictive prioritization of a plurality of predictive data entities, the computer-implemented method comprising:
 identifying, by one or more processors, a plurality of feature data objects for the plurality of predictive data entities;
 generating, by the one or more processors, a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features;
 generating, by the one or more processors, a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features;
 generating, by the one or more processors, a predicted prioritization score for each predictive data entity of the plurality of predictive data entities based at least in part on the multi-dimensional unsupervised machine learning space; and
 performing, by the one or more processors, one or more prediction-based actions based at least in part on each predicted prioritization score for a predictive data entity of the plurality of predictive data entities.

2. The computer-implemented method of claim 1, wherein identifying a feature data object of the plurality of feature data objects that is associated with a predictive data entity of the plurality of predictive data entities comprises:
 determining one or more format-specific input data groupings based at least in part on a predictive entity data object for the predictive data entity;
 determining one or more updated format-specific input data groupings based at least in part on the one or more format-specific input data groupings and one or more external feedback data objects;
 performing an initial pattern recognition traversal of each updated format-specific input data grouping of the one or more updated format-specific input data groupings to detect a set of initial features for the one or more updated format-specific input data groupings;
 performing one or more explanatory data analysis operations on the one or more updated format-specific input data groupings using the set of initial features to generate one or more updated features for the predictive entity data object; and
 generating the feature data object by processing the predictive entity data object in accordance with the one or more updated features.

3. The computer-implemented method of claim 2, wherein performing the one or more explanatory data analysis operations comprises:
 generating a group of numerical representation values for the set of initial features in relation to the predictive data entity;
 detecting one or more co-linear features of the set of initial features based at least in part on a distribution of the group of numerical representation values across the plurality of predictive data entities;
 detecting one or more missing-value features of the set of initial features based at least in part on a count of missing values for the set of initial features in across the plurality of predictive data entities; and
 generating the one or more updated features for the predictive entity data object based at least in part on the one or more co-linear features and the one or more missing-value features.

4. The computer-implemented method of claim 1, wherein generating the refined multi-input-type supervised machine learning model comprises:
 generating one or more initial multi-input-type supervised machine learning models based at least in part on the one or more labeled feature data objects;
 generating one or more refined features based at least in part on evaluating the one or more labeled feature data objects in relation to a prediction accuracy measure for each of the one or more initial multi-input-type supervised machine learning models;
 for each initial multi-input-type supervised machine learning model of the one or more initial multi-input-type supervised machine learning models, determining one or more model-related features of the one or more refined features;
 generating the one or more refined features based at least in part on each one or more model-related features for an initial multi-input-type supervised machine learning model;
 generating one or more model-related feature data objects based at least in part on the one or more refined features;
 generating an updated multi-input-type supervised machine learning model based at least in part on the one or more model-related feature data objects;
 generating one or more model testing outputs for the updated multi-input-type supervised machine learning model by testing the updated multi-input-type supervised machine learning model based at least in part on a subset of the one or more model-related feature data objects that fall outside a corresponding feature segment of the one or more labeled feature data objects for the updated multi-input-type supervised machine learning model;

performing one or more hyper-parameter tuning operations for the updated multi-input-type supervised machine learning model based at least in part on the one or more model testing outputs for the updated multi-input-type supervised machine learning model to generate a tuned candidate trained multi-input-type supervised machine learning model;

determining whether an accuracy metric for the tuned candidate trained multi-input-type supervised machine learning model is deemed optimal; and in response to determining that the accuracy metric for the tuned candidate trained multi-input-type supervised machine learning model is deemed optimal, generating the refined multi-input-type supervised machine learning model based at least in part on the tuned candidate trained multi-input-type supervised machine learning model.

5. The computer-implemented method of claim 1, wherein generating each predicted prioritization score for a predictive data entity of the plurality of predictive data entities comprises:

determining, based at least in part on the plurality of multi-dimensional entity mappings, one or more target entity clusters;

determining, for each refined feature of the one or more refined features, a measure of correlation across the one or more target entity clusters;

determining one or more target features of the one or more refined features based at least in part on each measure of correlation for a refined feature of the one or more refined features;

generating a prioritization machine learning model based at least in part on the one or more target features; and processing each predictive data entity of the plurality of predictive data entities using the prioritization machine learning model to generate the predicted prioritization score for the predictive data entity.

6. The computer-implemented method of claim 1, wherein performing the one or more prediction-based actions is performed based at least in part on one or more recommended actions for each predictive data entity of the plurality of predictive data entities and a recommended action ordering of each one or more recommended actions for a predictive data entity of the plurality of predictive data entities.

7. The computer-implemented method of claim 6, wherein each one or more recommended actions for a predictive data entity of the plurality of predictive data entities describes one or more genetic testing actions for a patient profile of a plurality of patient profiles.

8. The computer-implemented method of claim 7, wherein each recommended action ordering of the one or more recommended actions for a predictive data entity of the plurality of predictive data entities is determined based at least in part on a medical necessity hierarchy associated with the one or more recommended actions.

9. An apparatus for predictive prioritization of a plurality of predictive data entities, the apparatus comprising one or more processors and at least one memory including program code, the at least one memory and the program code configured to, with the one or more processors, cause the apparatus to at least:

identify a plurality of feature data objects for the plurality of predictive data entities;

generate a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features;

generate a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features;

generate a predicted prioritization score for each predictive data entity of the plurality of predictive data entities based at least in part on the multi-dimensional unsupervised machine learning space; and perform one or more prediction-based actions based at least in part on each predicted prioritization score for a predictive data entity of the plurality of predictive data entities.

10. The apparatus of claim 9, wherein identifying a feature data object of the plurality of feature data objects that is associated with a predictive data entity of the plurality of predictive data entities comprises:

determining one or more format-specific input data groupings based at least in part on a predictive entity data object for the predictive data entity;

determining one or more updated format-specific input data groupings based at least in part on the one or more format-specific input data groupings and one or more external feedback data objects;

performing an initial pattern recognition traversal of each updated format-specific input data grouping of the one or more updated format-specific input data groupings to detect a set of initial features for the one or more updated format-specific input data groupings;

performing one or more explanatory data analysis operations on the one or more updated format-specific input data groupings using the set of initial features to generate one or more updated features for the predictive entity data object; and generating the feature data object by processing the predictive entity data object in accordance with the one or more updated features.

11. The apparatus of claim 10, wherein performing the one or more explanatory data analysis operations comprises:

generating a group of numerical representation values for the set of initial features in relation to the predictive data entity;

detecting one or more co-linear features of the set of initial features based at least in part on a distribution of the group of numerical representation values across the plurality of predictive data entities;

detecting one or more missing-value features of the set of initial features based at least in part on a count of missing values for the set of initial features in across the plurality of predictive data entities; and generating the one or more updated features for the predictive entity data object based at least in part on the one or more co-linear features and the one or more missing-value features.

12. The apparatus of claim 9, wherein generating the refined multi-input-type supervised machine learning model comprises:

generating one or more initial multi-input-type supervised machine learning models based at least in part on the one or more labeled feature data objects;

generating one or more refined features based at least in part on evaluating the one or more labeled feature data objects in relation to a prediction accuracy measure for each of the one or more initial multi-input-type supervised machine learning models;

for each initial multi-input-type supervised machine learning model of the one or more initial multi-input-type supervised machine learning models, determining one or more model-related features of the one or more refined features;

generating the one or more refined features based at least in part on each one or more model-related features for an initial multi-input-type supervised machine learning model;

generating one or more model-related feature data objects based at least in part on the one or more refined features;

generating an updated multi-input-type supervised machine learning model based at least in part on the one or more model-related feature data objects;

generating one or more model testing outputs for the updated multi-input-type supervised machine learning model by testing the updated multi-input-type supervised machine learning model based at least in part on a subset of the one or more model-related feature data objects that fall outside a corresponding feature segment of the one or more labeled feature data objects for the updated multi-input-type supervised machine learning model;

performing one or more hyper-parameter tuning operations for the updated multi-input-type supervised machine learning model based at least in part on the one or more model testing outputs for the updated multi-input-type supervised machine learning model to generate a tuned candidate trained multi-input-type supervised machine learning model;

determining whether an accuracy metric for the tuned candidate trained multi-input-type supervised machine learning model is deemed optimal; and in response to determining that the accuracy metric for the tuned candidate trained multi-input-type supervised machine learning model is deemed optimal, generating the refined multi-input-type supervised machine learning model based at least in part on the tuned candidate trained multi-input-type supervised machine learning model.

13. The apparatus of claim 9, wherein generating each predicted prioritization score for a predictive data entity of the plurality of predictive data entities comprises:

determining, based at least in part on the plurality of multi-dimensional entity mappings, one or more target entity clusters;

determining, for each refined feature of the one or more refined features, a measure of correlation across the one or more target entity clusters;

determining one or more target features of the one or more refined features based at least in part on each measure of correlation for a refined feature of the one or more refined features;

generating a prioritization machine learning model based at least in part on the one or more target features; and processing each predictive data entity of the plurality of predictive data entities using the prioritization machine learning model to generate the predicted prioritization score for the predictive data entity.

14. The apparatus of claim 9, wherein performing the one or more prediction-based actions is performed based at least in part on one or more recommended actions for each predictive data entity of the plurality of predictive data entities and a recommended action ordering of each one or more recommended actions for a predictive data entity of the plurality of predictive data entities.

15. The apparatus of claim 14, wherein each one or more recommended actions for a predictive data entity of the plurality of predictive data entities describes one or more genetic testing actions for a patient profile of a plurality of patient profiles.

16. The apparatus of claim 15, wherein each recommended action ordering of the one or more recommended actions for a predictive data entity of the plurality of predictive data entities is determined based at least in part on a medical necessity hierarchy associated with the one or more recommended actions.

17. A computer program product for predictive prioritization of a plurality of predictive data entities, the computer program product comprising at least one non-transitory computer-readable storage medium having computer-readable program code portions stored therein, the computer-readable program code portions configured to:

identify a plurality of feature data objects for the plurality of predictive data entities;

generate a refined multi-input-type supervised machine learning model based at least in part on one or more labeled feature data objects of the plurality of feature data objects that are associated with a labeled subset of the plurality of predictive data entities, wherein the refined multi-input-type supervised machine learning model is associated with one or more refined features;

generate a multi-dimensional unsupervised machine learning space that comprises a plurality of multi-dimensional entity mappings of the plurality of predictive data entities, wherein the multi-dimensional unsupervised machine learning space is associated with a plurality of mapping dimensions each associated with a refined feature of the one or more refined features;

generate a predicted prioritization score for each predictive data entity of the plurality of predictive data entities based at least in part on the multi-dimensional unsupervised machine learning space; and perform one or more prediction-based actions based at least in part on each predicted prioritization score for a predictive data entity of the plurality of predictive data entities.

18. The computer program product of claim 17, wherein identifying a feature data object of the plurality of feature data objects that is associated with a predictive data entity of the plurality of predictive data entities comprises:

determining one or more format-specific input data groupings based at least in part on a predictive entity data object for the predictive data entity;

determining one or more updated format-specific input data groupings based at least in part on the one or more format-specific input data groupings and one or more external feedback data objects;

performing an initial pattern recognition traversal of each updated format-specific input data grouping of the one or more updated format-specific input data groupings to detect a set of initial features for the one or more updated format-specific input data groupings;

performing one or more explanatory data analysis operations on the one or more updated format-specific input data groupings using the set of initial features to generate one or more updated features for the predictive entity data object; and generating the feature data object by processing the predictive entity data object in accordance with the one or more updated features.

19. The computer program product of claim 18, wherein performing the one or more explanatory data analysis operations comprises:
generating a group of numerical representation values for the set of initial features in relation to the predictive data entity;
detecting one or more co-linear features of the set of initial features based at least in part on a distribution of the group of numerical representation values across the plurality of predictive data entities;
detecting one or more missing-value features of the set of initial features based at least in part on a count of missing values for the set of initial features in across the plurality of predictive data entities; and
generating the one or more updated features for the predictive entity data object based at least in part on the one or more co-linear features and the one or more missing-value features.

20. The computer program product of claim 17, wherein generating the refined multi-input-type supervised machine learning model comprises:
generating one or more initial multi-input-type supervised machine learning models based at least in part on the one or more labeled feature data objects;
generating one or more refined features based at least in part on evaluating the one or more labeled feature data objects in relation to a prediction accuracy measure for each of the one or more initial multi-input-type supervised machine learning models;
for each initial multi-input-type supervised machine learning model of the one or more initial multi-input-type supervised machine learning models, determining one or more model-related features of the one or more refined features;
generating the one or more refined features based at least in part on each one or more model-related features for an initial multi-input-type supervised machine learning model;
generating one or more model-related feature data objects based at least in part on the one or more refined features;
generating an updated multi-input-type supervised machine learning model based at least in part on the one or more model-related feature data objects;
generating one or more model testing outputs for the updated multi-input-type supervised machine learning model by testing the updated multi-input-type supervised machine learning model based at least in part on a subset of the one or more model-related feature data objects that fall outside a corresponding feature segment of the one or more labeled feature data objects for the updated multi-input-type supervised machine learning model;
performing one or more hyper-parameter tuning operations for the updated multi-input-type supervised machine learning model based at least in part on the one or more model testing outputs for the candidate trained multi-input-type supervised machine learning model to generate a tuned candidate trained multi-input-type supervised machine learning model;
determining whether an accuracy metric for the tuned candidate trained multi-input-type supervised machine learning model is deemed optimal; and
in response to determining that the accuracy metric for the tuned candidate trained multi-input-type supervised machine learning model is deemed optimal, generating the refined multi-input-type supervised machine learning model based at least in part on the tuned candidate trained multi-input-type supervised machine learning model.

* * * * *

UNITED STATES PATENT AND TRADEMARK OFFICE
CERTIFICATE OF CORRECTION

PATENT NO. : 11,977,985 B2
APPLICATION NO. : 17/096062
DATED : May 7, 2024
INVENTOR(S) : Darrel Naidoo et al.

It is certified that error appears in the above-identified patent and that said Letters Patent is hereby corrected as shown below:

In the Claims

In Column 40, Line 23, Claim 20, delete "candidate trained" and insert -- updated --, therefor.

Signed and Sealed this
First Day of July, 2025

Coke Morgan Stewart
*Acting Director of the United States Patent and Trademark Office*